United States Patent
Hirel et al.

(10) Patent No.: US 9,422,571 B2
(45) Date of Patent: Aug. 23, 2016

(54) INCREASED KERNEL PRODUCTIVITY OF PLANTS THROUGH THE MODULATION OF GLUTAMINE SYNTHETASE ACTIVITY

(71) Applicant: GENOPLANTE-VALOR, Evry (FR)

(72) Inventors: Bertrand Hirel, Versailles (FR); Pascual Perez, Chanonat (FR)

(73) Assignee: Genoplante-Valor, Evry (FR)

(*) Notice: Subject to any disclaimer, the term of this patent is extended or adjusted under 35 U.S.C. 154(b) by 243 days.

(21) Appl. No.: 13/829,878

(22) Filed: Mar. 14, 2013

(65) Prior Publication Data

US 2013/0185829 A1 Jul. 18, 2013

Related U.S. Application Data

(62) Division of application No. 12/444,030, filed as application No. PCT/IB2007/004195 on Oct. 9, 2007, now Pat. No. 8,426,704.

(30) Foreign Application Priority Data

Oct. 9, 2006 (EP) .................................. 06291570

(51) Int. Cl.
*A01H 1/00* (2006.01)
*C12N 15/00* (2006.01)
*C12N 15/82* (2006.01)
*C12N 9/00* (2006.01)
*A01H 5/00* (2006.01)

(52) U.S. Cl.
CPC ............ *C12N 15/8262* (2013.01); *C12N 9/93* (2013.01); *C12N 15/8261* (2013.01)

(58) Field of Classification Search
None
See application file for complete search history.

(56) References Cited

U.S. PATENT DOCUMENTS

| 7,589,257 | B2* | 9/2009 | Hershey et al. | 800/295 |
| 2005/0223443 | A1* | 10/2005 | Fox | 800/320.1 |
| 2007/0118916 | A1* | 5/2007 | Puzio et al. | 800/278 |

FOREIGN PATENT DOCUMENTS

WO WO 01/93465 A2 12/2001

OTHER PUBLICATIONS

Puzio et al., A_Geneseq Database, Accession No. AXE42092, US2007118916-A1, May 24, 2007.*
Li et al., GenEmbl Database, Accession No. X65928, Plant Mol. Biol. 23(2), 401-407, 1993.*
Fuentes et al., Journal of Experimental Botany, 52:358, 1071-1081, May 2001.*
International Search Report and Written Opinion for PCT/IB2007/004195 filed Oct. 9, 2007.
Andrews M et al: "Can genetic manipulation of plant nitrogen assimilation enzymes result in increased crop yield and greater N-use efficiency? An assessment"; Annals of Applied Biology; vol. 145, No. 1, 2004, pp. 25-40; XP002435261.
Limami Anis M et al: "Genetic and physiological analysis of germination efficiency in maize in relation to nitrogen metabolism reveals the importance of cytosolic glutamine synthetase." Plant Physiology (Rockville), vol. 130, No. 4, Dec. 2002; pp. 1860-1870; XP002435262.
Hirel Bertrand et al: "Towards a better understanding of the genetic and physiological basis for nitrogen use efficiency in maize"; Plant Physiology (Rockville); vol. 125, No. 3, Mar. 2001; pp. 1258-1270; XP002435263.
Miflin Ben J et al: "The role of glutamine synthetase and glutamate dehydrogenase in nitrogen assimilation and possibilities for improvement in the nitrogen utilization of crops"; Journal of Experimental Botany; vol. 53, No. 370; Apr. 2002; pp. 979-987; XP002435264.
Sakakibara H et al: "Molecular cloning of the family of glutamine synthetase genes from maize expression of genes for glutamine synthetase and ferredoxin-dependent glutamate synthase in photosynthetic and non-photosynthetic tissues"; Plant and Cell Physiology; vol. 33, No. 1; 1992; pp. 49-58; XP009084356.
& Database UniProt [Online]; Oct. 1, 1994; "Glutamine synthetase root isozyme 3 (EC 6.3.1.2) (Glutamate—ammonia ligase) (GS112)."; XP002436931.
& Database UniProt [Online]; Oct. 1, 1994; "Glutamine synthetase root isozyme 4 (EC 6.3.1.2) (Glutamate—ammonia ligase? (GS107)."; XP002436932.
Muhitch M: "Distribution of the glutamine synthetase isozyme GSp1 in maize (*Zea mays*)"; J Plant Physiol; vol. 160, 2003, pp. 601-605.

* cited by examiner

*Primary Examiner* — Phuong Bui
(74) *Attorney, Agent, or Firm* — Alston & Bird LLP

(57) ABSTRACT

The invention relates to a method for improving the kernel productivity of a maize plant, wherein said method comprises overexpressing in said plant at least one glutamine synthetase isoenzyme, in order to increase the number and/or size of kernels.

4 Claims, 8 Drawing Sheets

INCREASED KERNEL PRODUCTIVITY OF PLANTS THROUGH THE MODULATION OF GLUTAMINE SYNTHETASE ACTIVITY

CROSS REFERENCE TO RELATED APPLICATIONS

This application is a division of U.S. application Ser. No. 12/444,030, filed Jun. 22, 2009, now U.S. Pat. No. 8,426,704, which is a national stage application filed under 35 U.S.C. 371 of International Application No. PCT/IB2007/004195, filed Oct. 9, 2007, which claims priority to European Application No. 06291570.7, filed Oct. 9, 2006.

FIELD AND BACKGROUND OF THE INVENTION

The present invention relates to methods for controlling yield of plants, in particular cereal crops, preferably maize crops, through the modulation of glutamine synthetase (GS) activity.

The cereals including maize, wheat and rice account for 70% of worldwide food production. When such crops are grown for protein content, they require large quantities of nitrogenous fertilizers to attain maximal yields. In the past few years, there has been considerable interest in nitrogen use efficiency (NUE), which can be defined as the kernel yield per unit of nitrogen (N) in the soil and the N utilization efficiency (NutE), which is the yield per N taken up (Hirel and Lemaire, A. Basra, and S. Goyal, eds. (Haworth's Food Product Press. Binghamton, New-York), 15: 213-257, 2005). A number of physiological and agronomic studies have been undertaken to identify which are the limiting steps in the control of N uptake, assimilation and recycling during plant growth and development (Jeuffroy et al., J. Exp. Bot., 53: 809-823, 2002) including cereals such as maize (Hirel et al., Physiol. Plant, 124: 178-188, 2005b), rice (Yamaya et al., J. Exp. Bot., 53: 917-925, 2002) and more recently wheat (Kichey et al., New Phytol., 169: 265-278, 2006). Using maize as a model crop, Hirel et al. (aforementioned, 2005b) have investigated the changes in metabolite concentration and enzyme activities involved in N metabolism within a single leaf, at different stages of leaf growth and at different periods of plant development during the kernel-filling period. It was concluded that total N, chlorophyll, soluble protein content and GS activity are strongly interrelated and are indicators that mainly reflect the metabolic activity of individual leaves with regards to N assimilation and recycling, whatever the level of N fertilization.

Glutamine synthetase (GS; E.C.6.3.1.2) catalyzes the conversion of inorganic nitrogen (ammonium) into glutamine, according to the following reaction:

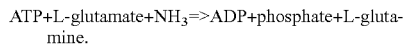

All of the N in a plant, whether derived initially from nitrate, ammonium ions, N fixation, or generated by other reactions within the plant that release ammonium (decarboxylation of glycine during photorespiration, metabolism of N transport compounds and the action of phenylalanine ammonia lyase) is channeled through the reactions catalyzed by GS. Thus, this enzyme is likely to be a major check point controlling plant growth and productivity (Miflin and Habash, J. Exp. Bot., 53(370): 979-87, 2002).

In maize, the putative role of GS for kernel productivity has also been highlighted using quantitative genetic approaches. QTLs for the leaf enzyme activity have been shown to be coincident with QTLs for yield (Hirel et al., Plant Physiol., 125: 1258-1270, 2001), and a positive correlation has been observed between kernel yield and GS activity (Gallais and Hirel, J. Exp. Bot., 55: 295-306, 2004). Further QTLs for GS gene loci have been identified in relation to remobilization of N from the leaf, stem and whole plant, post-anthesis N uptake (Gallais and Hirel, aforementioned, 2004) and germination efficiency (Limami et al., Plant Physiol., 130: 1860-1870, 2002). The importance of GS in controlling cereal productivity has recently been strengthened by a study performed in rice, in which a strong reduction in both growth rate and kernel yield was observed in a mutant deficient in cytosolic GS (Tabuchi et al., Plant J., 42: 641-655, 2005).

GS in higher plants including maize can be readily separated by standard chromatographic, localization and western blotting techniques into cytoplasmic (GS1) and plastidic (GS2) forms (Hirel and Lea, In: Plant Nitrogen, P. J. Lea and J. F. Morot-Gaudry, eds (INRA, Springer), pp. 79-99, 2001). However, this distinction is not as simple as was first thought, as although only one gene has been shown to encode the plastidic form, a small family of up to five genes is now known to encode the cytoplasmic form (Cren and Hirel, Plant Cell Physiol., 40: 1187-1193, 1999). Initial experiments indicated that the five cytoplasmic GS genes were differentially expressed in the roots, stems and leaves of maize (Sakakibara et al., Plant Cell Physiol., 33: 1193-1198, 1992; J. Biol. Chem., 271: 29561-29568, 1996; Li et al., Plant Mol. Biol., 23: 401-440, 1993). GS1-2, which is an important GS isoenzyme of the developing kernel, is abundant in the pedicel and pericarp, but has also been shown to be present in immature tassels, dehiscing anthers, kernel glumes, ear husks, cobs and stalks of maize plants (Muhitch et al., Plant Sci., 163: 865-872, 2002; Muhitch, J. Plant Physiol., 160: 601-605, 2003). Compared to the four other genes encoding GS1, Gln1-5 is expressed at a very low level in leaves, roots and stems (Sakakibara et al., aforementioned, 1992; Li et al., aforementioned, 1993). In a more recent study of maize leaves carried out by Hirel et al. (aforementioned, 2005b), it was shown that two of the five genes encoding GS1 (Gln1-3 and Gln1-4) were highly expressed regardless of the leaf age and the level of N fertilization, although there was an increase in Gln1-4 transcripts in the older leaves. It has been suggested that Gln1-4 encodes a GS isoform that is involved in the reassimilation of ammonium released during the remobilization of leaf proteins, whereas Gln1-3 encodes a GS isoform, which plays a house-keeping role during plant growth (Hirel et al., aforementioned, 2005a). The plastidic GS (GS2) encoded by Gln2 was only expressed in the early stages of plant development, presumably to reassimilate ammonium released during photorespiration, which is at a much lower rate in a $C_4$ plant compared with a $C_3$ plant (Ueno et al., Ann. Bot., 96: 863-869, 2005).

Despite the information available, as outlined above, concerning the expression of the five cytosolic GS1 genes in maize and the evidence of their importance from the demonstration of QTLs, the precise effect of the individual GS1 isoenzymes in the plant phenotype and kernel production is not known.

SUMMARY OF THE INVENTION

The inventors have now discovered the functional importance of the cytosolic GS isoenzyme products of the Gln1-3 and Gln1-4 genes in the control of kernel yield and its components in maize.

They have found that Gln1-3 plays a major part in the control of the number of kernels, while Gln1-4 plays a major part in the control of the size of the kernels. Further, they have observed that these genes act specifically on grain production, without affecting vegetative biomass production.

Gln1-3 encodes the cytosolic GS isoenzyme GS1-3. The cDNA sequence of Gln1-3 is available for instance in the GenBank database under the accession number X65928; the polypeptide sequence of GS1-3 is available for instance in the UniProtKB/Swiss-Prot database under the accession number P38561. A cDNA sequence of Gln1-3 is also represented herein as SEQ ID NO: 1, and the deduced polypeptide sequence is represented as SEQ ID NO: 2.

Gln1-4 encodes the cytosolic GS isoenzyme GS1-4. The cDNA sequence of Gln1-4 is available for instance in the GenBank database under the accession number X65929; the polypeptide sequence of GS1-4 is available for instance in the UniProtKB/Swiss-Prot database under the accession number P38562. A cDNA sequence of Gln1-4 is also represented herein as SEQ ID NO: 3, and the deduced polypeptide sequence is represented as SEQ ID NO: 4.

The invention provides a method for improving the kernel productivity of a maize plant, wherein said method comprises overexpressing in said plant a glutamine synthetase isoenzyme having at least 95% identity with the polypeptide SEQ ID NO: 2.

Unless otherwise specified, the percents of identity between two sequences which are mentioned herein are calculated from an alignment of the two sequences over their whole length.

According to a preferred embodiment of the invention, the kernel productivity is improved by increasing the number of kernels, and said glutamine synthetase is a GS1-3 isoenzyme having a serine at position 41 and an arginine at position 278. Preferably, said glutamine synthetase has the sequence SEQ ID NO: 2.

According to another preferred embodiment the kernel productivity is improved by increasing the size of kernels, and said glutamine synthetase is a GS1-4 isoenzyme having a proline at position 41 and a lysine at position 278. Preferably, said glutamine synthetase has the sequence SEQ ID NO: 4.

Advantageously, a method of the invention comprises overexpressing both the GS1-3 isoenzyme and the GS1-4 isoenzyme in a same plant, for increasing both the size and number of kernels.

The term "overexpressing" a glutamine synthetase isoenzyme in a plant, herein refers to artificially increasing the quantity of said active GS isoenzyme produced in said plant compared to a reference plant.

A preferred method for overexpressing a glutamine synthetase isoenzyme comprises introducing into the genome of said plant a DNA construct comprising a nucleotide sequence encoding said glutamine synthetase isoenzyme, placed under control of a promoter.

The instant invention also provides means for carrying out said overexpression.

This includes in particular recombinant DNA constructs for expressing a GS1-3 isoenzyme and/or a GS1-4 isoenzyme in a host-cell, or a host organism, in particular a plant cell or a plant. These DNA constructs can be obtained and introduced in said host cell or organism by the well-known techniques of recombinant DNA and genetic engineering.

Recombinant DNA constructs of the invention include in particular expression cassettes, comprising a polynucleotide encoding a glutamine synthetase isoenzyme, as defined above, under control of an heterologous promoter.

According to a particular embodiment, an expression cassette of the invention may comprise both a polynucleotide encoding a GS1-3 isoenzyme and a polynucleotide encoding a GS1-4 isoenzyme.

The heterologous promoter of the invention is any promoter functional in a plant cell, i.e., capable of directing transcription of a polynucleotide encoding a glutamine synthetase isoenzyme, as defined above, in a plant cell. The choice of the more appropriate promoter may depend in particular on the organ(s) or tissue(s) targeted for expression, and on the type of expression (i.e. constitutive or inducible) that one wishes to obtain.

A large choice of promoters suitable for expression of heterologous genes in plants, and in particular in maize, is available in the art. They can be obtained for instance from plants, plant viruses, or bacteria such as Agrobacterium. They include constitutive promoters, i.e. promoters which are active in most tissues and cells and under most environmental conditions, tissue or cell specific promoters which are active only or mainly in certain tissues or certain cell types, and inducible promoters that are activated by physical or chemical stimuli.

Non-limitative examples of constitutive promoters that are commonly used are the cauliflower mosaic virus (CaMV) 35S promoter, the nopaline synthase (Nos) promoter, the Cassava vein Mosaic Virus (CsVMV) promoter (Verdaguer et al., Plant Mol. Biol., 6: 1129-39, 1996), the rice actin promoter followed by the rice actin intron (RAP-RAI) contained in the plasmid pAct1-F4 (McElroy et al., Mol. Gen. Genet., 231(1): 150-160, 1991).

Non-limitative examples of organ or tissue specific promoters that can be used in the present invention include for instance High Molecular Weight (HMW) promoter which is kernel specific (Thomas and Flavell, Plant Cell., 2: 1171-80, 1990), or the leaf specific promoters as pPEPc promoter (Jeanneau et al., Biochimie, 84: 1127-1135, 2002), or the Rubisco small subunit promoter (rbcS) (Katayama et al., Plant Mol. Biol., 44: 99-106, 2000) which is specific of the bundle-sheath.

Inducible promoters include for instance drought stress responsive promoters, such as the rd29A promoter which comprises a dehydration-responsive element (Kasuga et al., Nature Biotech., 17: 287-291, 1999; Narusaka et al., Plant J., 34: 137-148, 2003), or the senescence specific SAG12 promoter (Noh and Amasino, Plant Mol. Biol., 41(2): 181-194, 1999).

The expression cassettes generally also include a transcriptional terminator, such as the 35S transcriptional terminator or Nos terminator (Depicker et al., J. Mol. Appl. Genet., 1: 561-73, 1982). They may also include other regulatory sequences, such as transcription enhancer sequences.

Recombinant DNA constructs of the invention also include recombinant vectors containing an expression cassette comprising a polynucleotide encoding a glutamine synthetase isoenzyme, as defined above, under transcriptional control of a suitable promoter. Said expression cassette may be a recombinant expression cassette of the invention, or a cassette wherein the polynucleotide encoding a glutamine synthetase is under control of its endogenous promoter.

A recombinant vector of the invention may include both a polynucleotide encoding a GS1-3 isoenzyme and a polynucleotide encoding a GS1-4 isoenzyme. These polynucleotides will advantageously be placed in separate expression cassettes under control of different promoters; for instance, a polynucleotide encoding a GS1-3 isoenzyme can be placed under control of the CsVMV promoter, and a polynucleotide encoding a GS1-4 isoenzyme can be placed under control of the rbcS promoter.

Recombinant vectors of the invention may also include other sequences of interest, such as, for instance, one or more marker genes, which allow for selection of transformed hosts.

Advantageously, the selectable marker gene is comprised between two Ds elements (i.e., transposons) in order for its removal at a later stage by interacting with the Ac transposase. This elimination system is known from one skilled in the art. By way of example, it has been described in Goldsbrough et al. (Biotechnology, 11:1286-1292, 1993).

The selection of suitable vectors and the methods for inserting DNA constructs therein are well known to persons of ordinary skill in the art. The choice of the vector depends on the intended host and on the intended method of transformation of said host. A variety of techniques for genetic transformation of plant cells or plants are available in the art for many plant species. By way of non-limitative examples, one can mention virus-mediated transformation, transformation by microinjection, by electroporation, microprojectile-mediated transformation, *Agrobacterium* mediated transformation (Ishida et al., Nat. Biotechnol., 14:745-750, 1996), and the like.

The term "plant" as used herein, includes dicotyledons as well as monocotyledons, and in particular those of agronomical interest, as cereal crops, such as wheat plant or rice plant, preferably maize plant.

The invention also comprises host cells containing a recombinant DNA construct of the invention. These host cells can be prokaryotic cells or eukaryotic cells, in particular plant cells, and preferably maize cells.

The invention also provides a method for producing a transgenic plant, in particular a maize plant, having an improved kernel productivity. Said method comprises transforming a plant cell (e.g., a maize cell) by a DNA construct of the invention and regenerating from said plant cell (e.g., maize cell) a transgenic plant (e.g., maize plant) overexpressing a GS1-3 isoenzyme and/or a GS1-4 isoenzyme.

According to a preferred embodiment or the method of the invention, it comprises transforming a plant cell, in particular a maize cell, by a recombinant vector of the invention comprising a polynucleotide encoding a GS1-3 isoenzyme, and by a recombinant vector of the invention comprising a polynucleotide encoding a GS1-4 isoenzyme, and regenerating from said plant cell (e.g., maize cell) a transgenic plant (e.g., maize plant) overexpressing a GS1-3 isoenzyme and GS1-4 isoenzyme.

According to another preferred embodiment or the method of the invention, it comprises transforming a plant cell, in particular a maize cell, by a recombinant vector of the invention comprising a polynucleotide encoding a GS1-3 isoenzyme and a polynucleotide encoding a GS1-4 isoenzyme, and regenerating from said plant cell (e.g., maize cell) a transgenic plant (e.g., maize plant) overexpressing a GS1-3 isoenzyme and GS1-4 isoenzyme.

The invention also comprises plants genetically transformed by a recombinant DNA construct of the invention, and overexpressing a GS1-3 isoenzyme and/or a GS1-4 isoenzyme. Preferably, said plants are transgenic maize plants, obtainable by a method of the invention, overexpressing a GS1-3 isoenzyme and/or a GS1-4 isoenzyme. In said transgenic plants a DNA construct of the invention is comprised in a transgene integrated (i.e., stably integrated) in the plant genome, so that it is passed onto successive plant generations. Thus the transgenic plants of the invention include not only the plants resulting from the initial transgenesis, but also their descendants, as far as they contain a recombinant DNA construct of the invention. The overexpression of a GS1-3 isoenzyme and/or a GS1-4 isoenzyme glutamine synthetase in said plants provides them an improved kernel productivity, when compared with a plant devoid of said transgene(s).

Accordingly, the invention provides a transgenic plant or an isolated organ or tissue thereof comprising, stably integrated in its genome, a recombinant expression cassette comprising a polynucleotide encoding a GS1-3 isoenzyme, and/or a polynucleotide encoding a GS1-4 isoenzyme.

The invention also encompasses isolated organs or tissues of said transgenic plants (such as seeds, leafs, flowers, roots, stems, ears) containing a recombinant expression cassette of the invention.

Foregoing and other objects and advantages of the invention will become more apparent from the following detailed description and accompanying drawings. It is to be understood however that this foregoing detailed description is exemplary only and is not restrictive of the invention.

BRIEF DESCRIPTION OF THE DRAWINGS

FIG. 4A is a 2-D gel of proteins extracted from the leaves of WT maize plants. The rectangular box identifies the region of the gel corresponding to the pI range and molecular mass range characteristic of GS proteins. Enlarged views of the 2-D gel region identified in FIG. 4A are shown in FIG. 4B, with individual gels containing protein extracted from WT maize plants and gln1-4, gln1-3, and gln1-3/gln1-4 deficient maize plants. The arrows indicate protein spots corresponding to GS1-3, GS1-4, and GS2 proteins, as determined using liquid chromatography-tandem mass spectrometry (LC-MS/MS). FIG. 4C shows alignments of protein sequences from various GS proteins. The aligned regions reveal differences in the GLN1-3 and GLN1-4 protein sequences that can be used to distinguish the proteins.

FIG. 10A is a bar graph showing the total leaf GS activity of each line. FIG. 10B is a bar graph showing kernel yield of each line. FIG. 10C is a bar graph showing the total dry weight of shoot vegetative parts of each line. FIG. 10D is a scatter plot showing the relationship between leaf GS activity (abscissa) and kernel yield (ordinate) for the lines.

DETAILED DESCRIPTION OF THE INVENTION

Example 1

Characteristics of the Gln1-3:: and Gln1-4:: Mu-Insertion Events

Knock out mutants of Gln1-3 and Gln1-4 genes have been isolated using the maize Mutator (Mu) system (Hanley et al., Plant J., 23: 557-566, 2000). The insertion lines of Gln1-3::Mu and Gln1-4::Mu have undergone extensive backcrossing to the wild type non-Mu line and homozygous, heterozygous and null mutant lines have been obtained. In addition, a double mutant (gln1-3/gln1-4) of the Gln1-3 and Gln1-4 genes has been produced.

Figure 1:
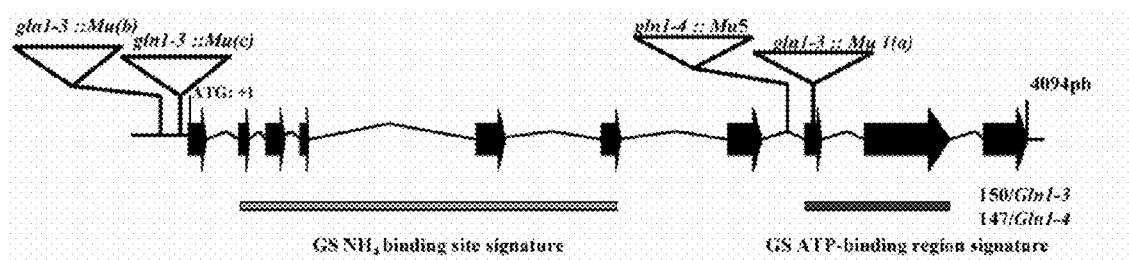
FIG. 1 depicts the structure of the maize Gln1-3 and Gln1-4 genes. Exons are shown as arrows and introns are shown as thin lines. Shaded lines located beneath the gene structure identify the relative positions of the GS-$NH_4^+$-binding site signature and the GS-ATP-binding region signature. Known Mutator (mu) insertion sites are represented with triangles.

The position of the Mutator elements inserted within the Gln1-3 and Gln1-4 genes is shown in FIG. 1

For clarity and as the Gln1-3 and Gln1-4 genes show high sequence similarity, they are shown as a single structure. The Gln1-3 and Gln1-4 gene structure and exon sizes were determined by sequencing genomic DNA PCR products using primers designed from the corresponding cDNA sequences (Li et al., aforementioned, 1993); the Mu-insertion sequences and the rice genomic clone AC105364.

The maize Gln1-3 and Gln1-4 genes consist of 10 exons (black arrows), ranging in size from 40 bp to 252 bp, and 9 introns (black lines). The size of the last exon was 150 bp in Gln1-3 and 147 bp in Gln1-4. The introns and exon structure is drawn to scale. The gene numbering starts with the ATG codon (1 bp) and continues to the stop codon (position 3857 bp).

The two Mu-insertion events are indicated by triangles (not to scale).

Also shown is the relative position of the $GS-NH_4^+$-binding site signature and the GS-ATP-binding region signature.

Sequence analysis of the flanking regions surrounding the Mu-elements indicated that in the case of Gln1-3::Mu1 the insertion had occurred within exon 8 and in the case of Gln1-4::Mu5 the insertion had occurred within the intron separating exon 7 and exon 8.

Example 2

Glutamine Synthetase Expression and Activity in Gln1-3, Gln1-4 and Double Mutants Plant Material Seeds of the three GS1-deficient mutants, or the corresponding WT were first sown on coarse sand and after 1 week, when 2 to 3 leaves had emerged, were transferred either to hydroponic culture for root harvesting, or to soil for leaf harvesting. For the hydroponic culture, 12 plants (3 for the WT and 3 for each mutant) were randomly placed on a 130 L aerated culture unit. The experiment was performed in triplicate for each line and plants were grown for 18 days in a growth chamber with a 16/8 light/dark period. A photosynthetic photon flux density of 400 µmol $m^{-2}$ $s^{-1}$ was provided by metal halide lamps. The relative humidity was maintained at 60% of saturation. Plants were harvested at the 10-11 leaf stage between 9 to 12 am and separated into young leaves (3 youngest leaves) and roots. The root samples were immediately placed in liquid $N_2$ and then stored at −80° C. until further analysis.

Three plants of the three mutants were transferred to pots (diameter and height of 30 cm) containing clay loam soil and at the 10-11 leaf stage, the 3 youngest fully expanded leaves were harvested and pooled for the vegetative stage (VS) samples. The leaf below the ear was harvested at later stages of plant development including 15 days after silking (15DAS) and 55 days after silking (55DAS). The leaf, below the ear, was selected since it has been shown to provide a good indication of the source sink transition during grain filling (Hirel et al., aforementioned, 2005a,b; Martin et al., New Phytol., 167: 483-492, 2005). No major variations in N metabolite content and enzyme activity within a single leaf blade have been observed until the latest stages of leaf development. Therefore, it has been concluded that the entire leaf blade can be used for measuring physiological traits related to N metabolism (Hirel et al., aforementioned, 2005b). Leaf samples were harvested between 9 am to 12 am and frozen in liquid $N_2$, ground to a homogenous powder and stored at −80° C. for use in subsequent RNA, protein and metabolite analyses.

In the hydroponic culture, plants were grown on a complete nutrient solution containing 10 mM $NO_3^-$ as the sole N source (Coïc and Lesaint, Hortic. Française, 8: 11-14, 1971). The nutrient solution was replaced daily. In the glasshouse, plants were watered daily with a complete nutrient solution containing 10 mM $NO_3^-$ as the sole N source (Coïc and Lesaint, aforementioned, 1971). For both growth methods, the complete nutrient solution contained 1.25 mM K$^+$, 0.25 mM Ca$^{2+}$, 0.25 mM Mg$^{2+}$, 1.25 mM H$_2$PO$_4^-$, 0.75 mM SO$_4^{2-}$, 21.5 µM Fe$^{2+}$ (Sequestrene; Ciba-Geigy, Basel, Switzerland), 23 µM B$^{3+}$, 9 µM Mn$^{2+}$, 0.3 µM Mo$^{2+}$, 0.95 µM Cu$^{2+}$ and 3.5 µM Zn$^{2+}$.

Glutamine Synthetase Protein Expression

The GS isoenzyme protein content of roots and leaves of the WT and three mutants was examined following one dimensional polyacrylamide gel electrophoresis and Western blot analysis, using antibodies raised against GS2 and GS1. This technique provides a reliable method of estimating the relative amounts of both GS1 and GS2 in a crude protein extract of maize leaves and roots (Becker et al., Planta, 211: 800-806, 2000).

Proteins were extracted from frozen leaves and roots powder obtained as described above, in cold extraction buffer containing 50 mM Tris-HCl pH 7.5, 1 mM EDTA, 1 mM MgCl2, 0.5% (w/v) PVP, 0.1% (v/v) 2-mercaptoethanol and 4 mM leupeptin, and separated by SDS-PAGE (Laemmli, Nature, 227: 680-685, 1970). The percentage of polyacrylamide in the gels was 10% and equal amounts of protein (10 µg) were loaded onto each track. Proteins were electrophoretically transferred to nitrocellulose membranes for Western blot analysis. GS1 and GS2 polypeptides were detected using polyclonal antisera raised either against GS2 of tobacco (Hirel et al., Plant Physiol., 74: 448-450, 1984), or against GS1 from *Phaseolus vulgaris* root nodules (Cullimore and Miflin, J. Exp. Bot., 35: 581-587, 1984). Soluble protein was determined using a commercially available kit (Coomassie Protein assay reagent, Biorad, München, Germany) using bovine serum albumin as a standard.

Figure 2:
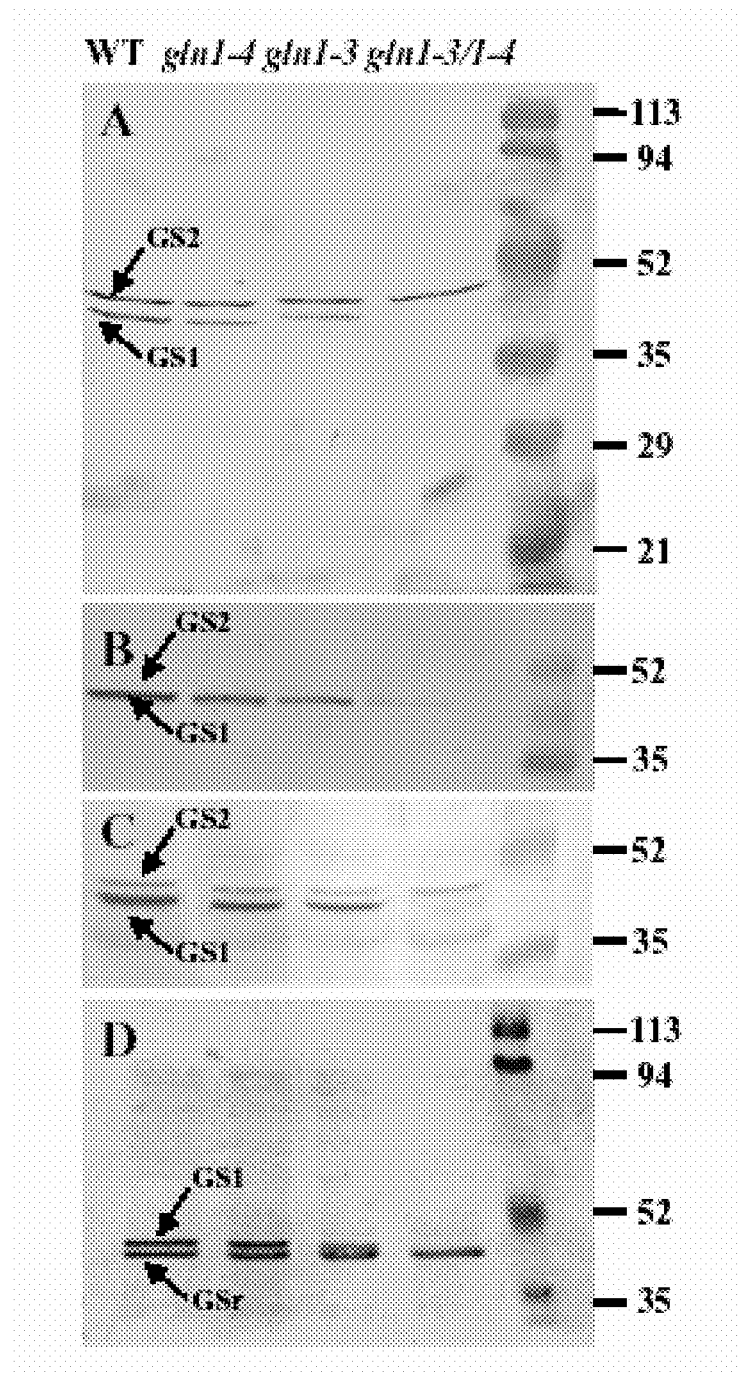
FIG. 2 depicts Western blot analysis of the GS subunit composition of: (A) leaves harvested at vegetative stage (VS), stained with tobacco GS antibodies; (B) of leaves harvested at VS, stained with *Phaseolus vulgaris* GS antibodies; (C) of leaves harvested at 55 days after silking (55DAS), stained with tobacco GS antibodies; and (D) of roots harvested at VS, stained with tobacco GS antibodies (D). Each blot includes samples from wild type (WT) maize plants and gln1-3, gln1-4, and gln1-3 and gln1-4 deficient maize plants. The upper band (molecular mass of 44 kD) corresponds to the plastidic GS (GS2) subunit, and the lower band (molecular mass of 39 kD) correspond to the cytosolic GS (GS1) subunit. The position of protein molecular weight markers is shown on the right.

The results are shown in FIG. 2.

Legend of FIG. 2:

Western blot analysis of the GS subunit composition of leaves harvested at VS, using tobacco GS antibodies (A), of leaves harvested at VS, using *Phaseolus vulgaris* GS antibodies (B), of leaves harvested at 55DAS, using tobacco GS antibodies (C), and of roots harvested at VS, using tobacco GS antibodies (D).

On the right side of the panels is shown the position of the protein molecular mass markers.

WT=wild type
gln1-3=gln1-3 deficient mutant
gln1-4=gln1-4 deficient mutant
gln1-3/1-4=gln1-3 and gln1-4 deficient mutant In the leaves of WT plants at VS, two polypeptides of similar relative abundance were detected, using the tobacco GS antibodies. The 44 kD polypeptide corresponds to the plastidic form of GS (GS2) whereas the 40 kD polypeptide corresponds to the cytosolic form of GS (GS1). In the gln1-3 and gln1-4 mutants, a decrease in the amount of GS1 protein was observed, which was more pronounced in the former. In the gln1-3/gln1-4, the GS1 protein was barely detectable. Similar amounts of GS2 protein were visible in the WT and in all three mutants (FIG. 2A). The decrease in GS1 protein contents of the gln1-3, gln1-4 and gln1-3/gln1-4 mutants at the VS, was confirmed using antibodies raised against *Phaseolus vulgaris* root nodule GS. However, since this antibody preparation is apparently more specific for cytosolic GS (GS1), GS2 protein was less readily visible on the Western blot (FIG. 2B). When the GS proteins were analyzed in the leaves at 55DAS, using the tobacco antibodies, a similar pattern of decrease in GS1 protein content was obtained in the mutants. However, at this later stage of plant development, the amount of GS2 protein isolated from all four lines was much lower (FIG. 2C).

In the root tissue of WT plants, two polypeptides of 38 and 40 kD corresponding to two cytosolic forms of GS (GSr and GSl, respectively), were detected (FIG. 2D). As already described by Sakakibara et al. (aforementioned, 1992), the upper band corresponds to a GS1 protein of a similar size to that found in the leaves, whereas the lower band is a root-specific cytosolic GS (GSr). A small decrease in the amount of the GS1 (40 kD) polypeptide was just visible in the gln1-4 mutant, whilst a considerable decrease was clearly detectable in the gln1-3 mutant. In the gln1-3/gln1-4 double mutant, the GS1 (40kD) polypeptide was not detected. Similar amounts of the GSr (38 kD) polypeptide were detected in the WT and in all three mutants (FIG. 2D).

Glutamine Synthetase Protein Activity

The GS isoenzyme activity content (the relative proportions of plastidic and cytosolic GS activities) of the WT and the three mutants was examined following ion exchange chromatography and enzymatic assays, using plants at the VS.

Proteins were extracted from frozen leaves and roots powder obtained as described in Example 1, in cold extraction buffer containing 100 mM TEA, 1 mM EDTA, 10 mM MgSO$_4$, 5 mM glutamic acid, 10% (v/v) ethylene glycol, 6 mM DTT, pH 7.6. Extracts were then centrifuged at 10 000 g for 15 min at 4° C. Separation on a Mono Q anion exchange column (Amersham Pharmacia Biotech) attached to an HPLC (DX 500; Dionex (UK) Ltd. Camberley, Surrey, UK) was performed as described by Habash et al. (Ann. Appl. Biol., 138: 83-89, 2001), except that a 0.1-0.7 M NaCl linear gradient was used for elution and 1 ml fractions were collected.

Glutamine synthetase (GS) activity was measured according to the method of Lea et al. (1999) for the transferase reaction and O'Neal and Joy (Archiv. Biochem. Biophys., 159: 113-122, 1973) for the synthetase reaction.

Figure 3:
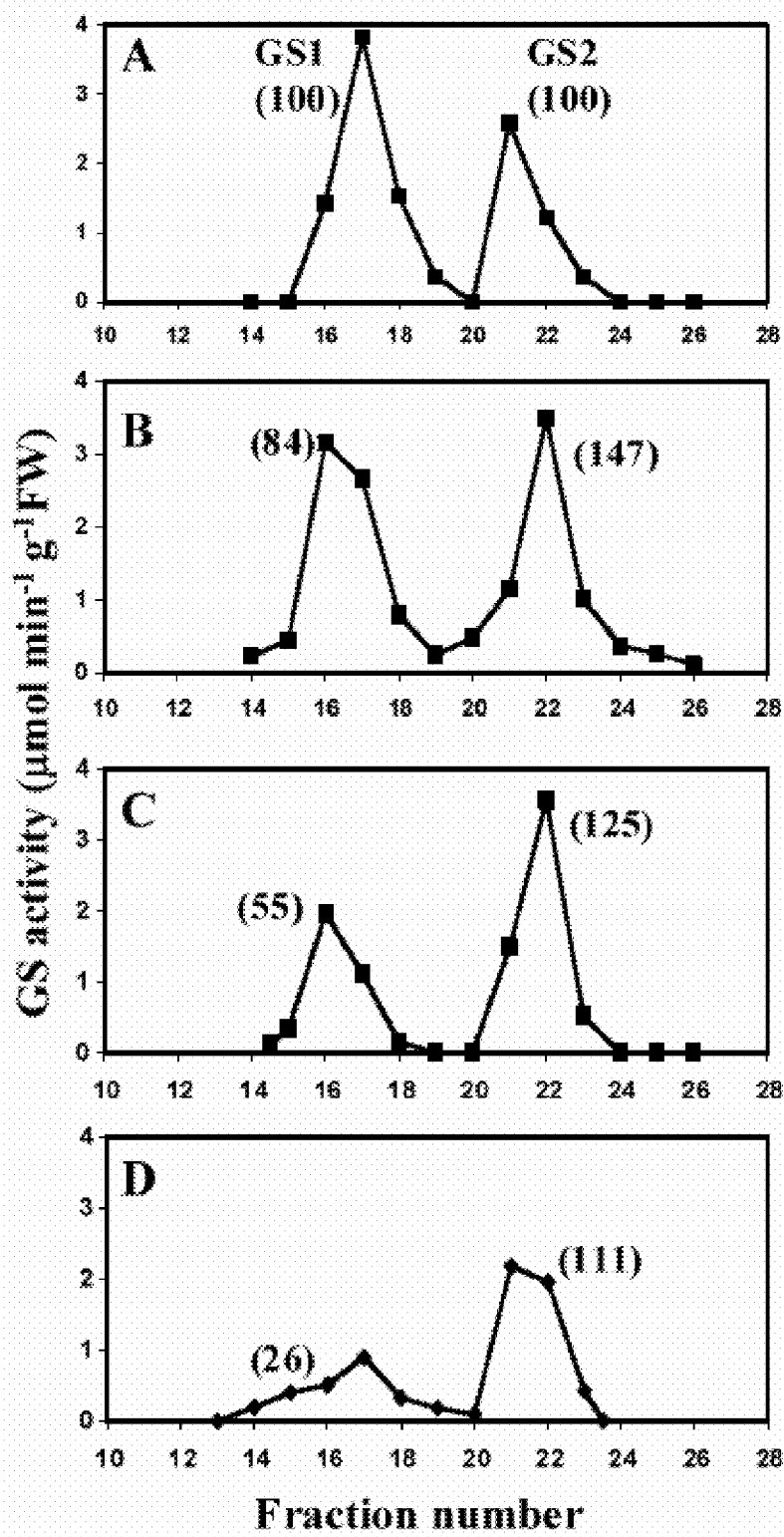
FIG. 3 depicts the GS activity of leaf extracts following separation by ion exchange chromatography. The leaf extracts were from (A) WT maize, (B) gln1-4 deficient maize, (C) gln1-3 deficient maize, and (D) gln1-3/gln1-4 deficient maize. The first peak of GS activity corresponds to cytosolic GS (GS1) and the second peak corresponds to plastidic GS (GS2).

The results obtained from leaf material with three independent extractions are shown in FIG. 3.

Legend of FIG. 3:

Ion exchange chromatography of GS activity in leaf extracts from WT (A), gln1-4 (B), gln1-3 (C) and gln1-3/gln1-4 (D). The first peak of GS activity corresponds to cytosolic GS (GS1) and the second peak to plastidic GS (GS2).

The relative amounts of GS1 and GS2 activity indicated in brackets was calculated using as a maximum, the value measured for the amount of GS1 and GS2 activities in the WT.

Compared to the WT (FIG. 3A), a 16% decrease in GS1 activity was observed in the gln1-4 mutant (FIG. 3B). The decrease in GS1 activity was higher in the gln1-3 mutant (45%) (FIG. 3C). Only 26% of the WT GS1 activity remained in the gln1-3/gln1-4 mutant (FIG. 3D). Interestingly an increase in GS2 activity ranging from 11 to 47% was observed in all three mutants (FIG. 3B-D).

Compared to the WT, root GS activities in the three mutants measured using the synthetase reaction at the VS were similar (3.2±0.06 µmol. min-1. g-1 DW for the WT, 3.4±0.3 for the gln1-4 mutant, 2.8±0.05 for the gln1-3 mutant and 3.1±0.05 for the gln1-3/gln1-4 mutant). This result indicates that root GS activity is mostly represented by the GSr protein which is encoded by the Gln1-1 gene, the mRNA of which is most abundantly expressed in roots.

Identification of GS Protein Sequences

Using plants harvested at the VS, leaf proteins extracted from the WT, the gln1-3, the gln1-4 and the gln1-3/gln1-4 mutant as above described, were separated by 2-D gel electrophoresis.

Figure 4:
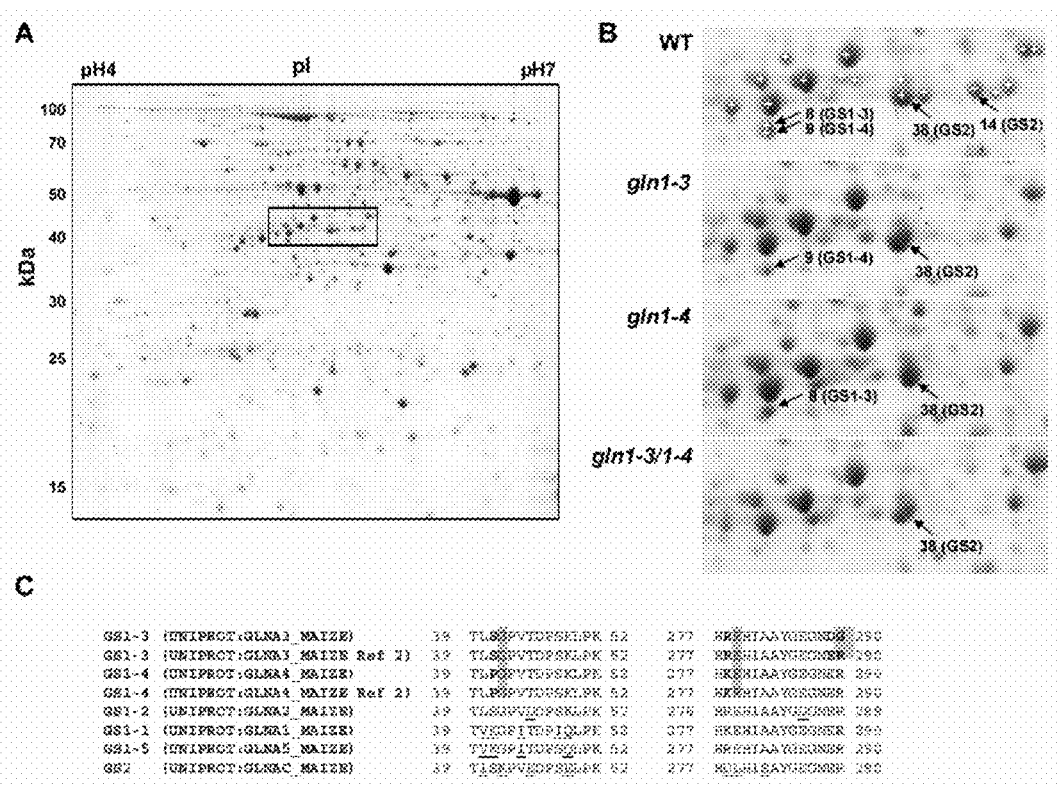
FIGS. 4A-C depict results obtained from 2-D gel electrophoresis and liquid chromatography-tandem mass spectrometry (LC-MS/MS) analysis of protein extracts from WT and mutant maize plants.

The 2-D gel of proteins extracted from the leaves of the WT is shown in FIG. 4A.

To unambiguously demonstrate that the corresponding GS protein was lacking in the gln1-3, gln1-4 and gln1-3/gln1-4 mutants, thirty-six protein spots in the range of the pI and molecular mass (MM) of GS from said region, were analyzed by liquid chromatography-tandem mass spectrometry (LC-MS/MS). The results are shown in FIG. 4B.

Protein identification revealed that out of these 36 spots, four of them (spots 8, 9, 14 and 38) contained a GS protein.

By comparison with the protein profile of the WT, it was observed that the gln1-3 mutant and the gln1-4 mutant were lacking spots 8 and 9 respectively and that they were both absent in the gln1-3/gln1-4 mutant. Spots 8 and 9 were very close to each other and exhibited a partial overlap. They had the same apparent pI but slightly differed by their apparent MM.

This finding is not surprising, because according to the sequences of the genes isolated by Li et al (aforementioned, 1993), GS1-3 and GS1-4 proteins have the same pI and exhibit only a 188 D difference in their mass. Both products of the allelic forms isolated by Sakakibara et al. (aforementioned, 1992), (respectively GS112 and GS107 for GS1-3 and GS1-4), have one more basic amino acid, and thus also exhibit similar pI.

Two sites of sequence polymorphism were used to distinguish between the GS1-3 and GS1-4 proteins from each other. The results are shown in FIG. 4C.

Legend of FIG. 4C:

Entry names of the sequence in the UNIPROT Database are given. Ref 2 of GS1-3 and GS1-4 refer to the allelic form sequenced by Sakakibara et al. (aforementioned, 1992). Positions are relative to the first methionine for all GS except for GS2, where it is relative to the first amino acid after the signal peptide. Shaded background shows the differences between GS1-3 and GS1-4 and between GS1-3 allelic forms. Differences between GS1-3 and GS1-4 on one hand and the rest of GS proteins on the other hand are underlined.

The sequences alignment shows that amino acid at position 41 is a serine in GS1-3 and a proline in GS1-4, and the amino acid at position 278 is an arginine in GS1-3 and a lysine in GS1-4. Peptides containing these sites of polymorphism were identified: TLSGPVTDPSK (SEQ ID NO: 5) (and the mis-cleaved TLSGPVTDPSKLPK (SEQ ID NO: 6)) allowed the identification of GS1-3, while TLPGPVTDPSK (SEQ ID NO: 7) (and TLPGPVTDPSKLPK (SEQ ID NO: 8)) allowed the identification of GS1-4 according to the S/P polymorphism at position 41, and HREHIAAYGEGNER (SEQ ID NO: 9) and HKEHIAAYGEGNER (SEQ ID NO: 10) allowed the identification of GS1-3 and GS1-4 proteins respectively according to the R/K polymorphism at position 278. It should be noted that the peptide HREHIAAYGEGNER (SEQ ID NO: 9) is similar to the allelic form of GS1-3 sequenced by Sakakibara et al. (aforementioned, 1992), but not to that sequenced by Li et al. (aforementioned, 1993), in which the two last amino acids of the peptide, ER, are substituted by DG.

Example 3

Phenotype and Kernel Production of the GS1 Deficient-Mutants

Kernel yield, its components, and the N content of different parts of the plant at stages of development from Bilking to maturity were determined according to the method described by Martin et al. (aforementioned, 2005).

To determine the impact of the mutations on plant phenotype and kernel production, plants were grown in a glasshouse on soil and watered daily with a nutrient solution containing 10 mM $NO_3^-$ (N suboptimal conditions) described by Coïc and Lesaint (aforementioned, 1971). Plants were harvested at maturity, and total N content was measured using the Dumas combustion method.

Shoot and Ear Dry Weight (DW) Accumulation in GS1-Deficient Mutants

Figure 5:
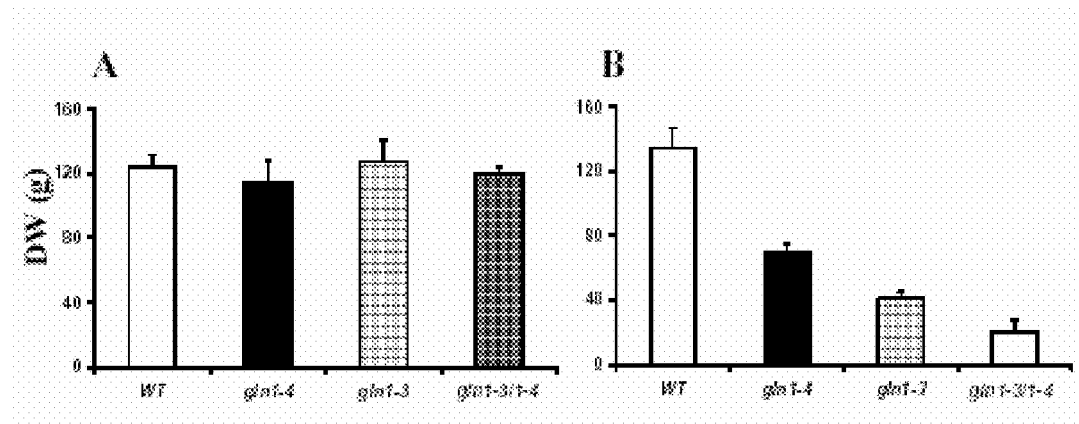
FIGS. 5A-B are bargraphs that depict (A) the total dry weight of shoot vegetative parts and (B) total ear dry weight from WT maize plants and gln1-3, gln1-4 and gln1-3/gln1-4 deficient maize plants. Ord=Dry weight (DW) in gram (g). Values are the mean±SE of three individual plants.

Total dry weight of shoot vegetative parts (A) and total ear dry weight (B) of WT, gln1-3, gln1-4 and gln1-3/gln1-4 are shown in FIG. 5.

Legend of FIG. 5:

Ord=Dry weight (DW) in gram (g)

Values are the mean±SE of three individual plants.

No significant differences were seen in the dry matter production of the vegetative parts of the shoot (FIG. 5A). In contrast, a major decrease in the dry matter content of the ear was observed, which when compared to the WT was 68% for gln1-3, 48% for gln1-4 mutant and 84% for the gln1-3/gln1-4 mutant. A reduction of ear size was observed in gln1-3 and gln1-4 mutants, and was even more severe in the gln1-3/gln1-4 mutant (FIG. 5B).

Phenotype of the Ear in GS1-Deficient Mutants

Figure 6:
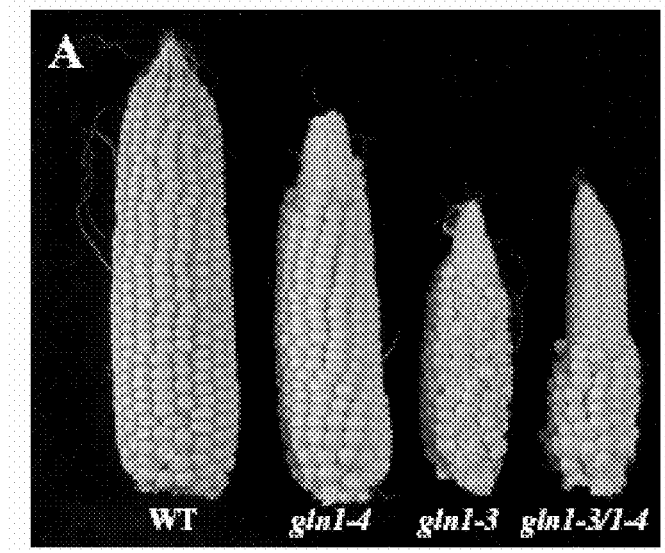
FIG. 6 depicts an image of ears of corn obtained from WT maize plants and gln1-4, gln1-3 and gln1-3/gln1-4 deficient maize plants.

Ears of WT, gln1-4, gln1-3 and gln1-3/gln1-4 of maize plants (line B73) are shown in FIG. 6.

In both gln1-3 and gln1-4 mutants, a strong reduction in kernel yield was observed, which was more important in the former, thus confirming the phenotype shown in FIG. 6.

The main components of kernel yield for the three GS mutants grown under N suboptimal conditions are presented in Table 1.

TABLE 1

|  | Grain Yield (g) | Grain Number | Thousand Kernels Weight (g) | Grain N content (% DW) |
|---|---|---|---|---|
| WT (line B73) | 117 ± 15 (100) | 464 ± 63 (100) | 252 ± 12 (100) | 2.10 ± 0.12 (100) |
| gln1-4 | 59 ± 4.5 (50)$^a$ | 331 ± 25 (71)$^a$ | 178 ± 11 (70)$^a$ | 2.49 ± 0.04 (118)$^a$ |
| gln1-3 | 27 ± 9.5 (23)$^a$ | 120 ± 43 (26)$^a$ | 220 ± 5 (87)$^a$ | 2.66 ± 0.07 (126)$^a$ |
| gln1-3/1-4 | 14 ± 8 (12)$^a$ | 89 ± 51 (19)$^a$ | 158 ± 4 (63)$^a$ | 2.48 ± 0.08 (118)$^a$ |

Each value is the mean ± SE obtained from three individual plants.
The values indicated in parentheses are expressed as percentage of the value in the WT.
$^a$Significantly different from the WT at 0.05 probability level.

In the gln1-3/gln1-4 mutant, the kernel yield was reduced to only 12% of the wild type. In gln1-4, there was a greater reduction in kernel weight but a larger kernel number, when compared to gln1-3. In the gln1-3/gln1-4 mutant, both yield components were strongly reduced compared to the WT and the two single mutants. Compared to the WT, an approximately 20% increase in N kernel content was observed in the three mutants.

Example 4

Physiology of the GS1 Deficient-Mutants

The effect of decreased levels of GS1 activity on representative markers of leaf N and C metabolism (Hirel et al., aforementioned, 2005b), was examined in the three maize mutants.

Metabolite Extraction and Analyses

Metabolites were quantified in maize plants at VS. Lyophilized plant material was used for metabolite extraction. $NH_4^+$ and amino acids were extracted with 2% 5-sulfosalicylic acid (10 mg DW, $ml^{-1}$; Ferrario-Méry et al., Plant Physiol., 117: 293-302, 1998). Total amino acid content and individual amino acid composition was determined by ion-exchange chromatography on pooled samples extracted from equal dry weights. Total free amino acids were determined by the Rosen colorimetric method, using leucine as a standard (Rosen, Arch. Biochem. Biophys., 67(1): 10-15, 1957). The composition of individual amino acids was performed by ion-exchange chromatography followed by detection with ninhydrin using the AminoTac JLC-500/V amino acid analyzer according to the instructions of the manufacturer (JEOL [Europe], Croissy-sur-Seine, France). Free $NH_4^+$ was determined by the phenol hypochlorite assay (Berthelot reaction), which provides reliable data for comparative studies when the concentration of $NH_4^+$ is low, although a more precise quantification can be obtained by other methods (Husted et al., Physiol. Plant, 109: 167-179, 2000). Sucrose, glucose, fructose, starch were extracted with 1 M $HClO_4$ (1 ml per 5 to 10 mg DW of plant material) as described by Ferrario-Méry et al. (aforementioned, 1998). The soluble sugars (glucose, fructose and sucrose) were measured enzymatically using a commercially available kit assay (Boehringer Mannheim, Germany).

The results are shown in Table 2.

TABLE 2

Metabolite Concentration ($\mu$mol g $DW^{-1}$) and Total N (%)

| Metabolites | WT | gln1-4 | gln1-3 | gln1-3/1-4 |
|---|---|---|---|---|
| $NH_4^+$ | 24.22 ± 1.9 | 41.5 ± 3.1[a] | 43.6 ± 2.3[a] | 99.15 ± 11.4[a] |
| $NO_3^-$ | 64 ± 2.5 | 57.3 ± 11.4 | 61.5 ± 6.7 | 64 ± 2.1 |
| Soluble Sugars | 2350 ± 110 | 1930 ± 220 | 1980 ± 410 | 2030 ± 306 |
| Amino Acids | 73.20 ± 17 | 93.03 ± 6.5 | 83.1 ± 3 | 98.9 ± 30 |
| Total N | 4.36 ± 0.08 | 4.31 ± 0.1 | 4.28 ± 0.1 | 4.42 ± 0.3 |

[a]Values are the mean of three plants ± SD. For Soluble Sugars, sucrose represented 98% of the total.
[a]Significant changes at the 0.05 probability level compared to the WT.

Table 2 shows that the reduction in GS1 activity in gln1-3 and gln1-4 mutants resulted in an almost 2-fold increase in the quantity of free $NH_4^+$ in the leaves, whilst in the gln1-3/gln1-4 mutant, this amount was approximately four times higher compared to the wild type. At the VS, no significant differences in the $NO_3^-$, soluble sugars, free amino acids (both qualitatively and quantitatively) and total N contents of the leaves were observed between the WT and the three mutants. Although less marked, an increase in the quantity of free $NH_4^+$ was still observed 15DAS in the three GS mutants. At this stage of plant development, the relative concentrations of $NO_3^-$, amino acids and soluble sugars were also reduced but no significant changes between the WT and the mutants were detected (data not shown). As already reported earlier (Hirel et al., aforementioned, 2005b), the amounts of $NO_3^-$, $NH_4^+$ and soluble sugars in the leaves 55DAS were at least four times lower in both the WT and the three GS mutants. However, no marked differences were observed between the WT and the three mutants.

At the 55DAS stage, the effect of the reduction in GS1 activity on the levels of amino acids and N were investigated. The results are shown in Table 3.

TABLE 3

Amino Acid Concentration ($\mu$mol g $DW^{-1}$) and Proportions (%)[a]

| Amino Acid | WT | gln1-4 | gln1-3 | gln 1-3/1-4 |
|---|---|---|---|---|
| Asp | 1.85 ± 0.52 (11) | 4.19 ± 1.24 (10) | 1.61 ± 0.31 (6) | 1.07 ± 0.24 (3) |
| Asn | 0.58 ± 0.07 (3) | 6.18 ± 1.61 (15)[b] | 1.58 ± 0.10 (6)[b] | 11.91 ± 1.60 (29)[b] |
| Glu | 1.03 ± 0.15 (6) | 2.27 ± 0.22 (5)[b] | 3.56 ± 0.55 (14)[b] | 9.57 ± 3.88 (23)[b] |
| Gln | 3.56 ± 1.01 (21) | 6.85 ± 1.63 (16)[c] | 3.57 ± 0.10 (14)[c] | 1.96 ± 0.44 (5)[c] |
| Ala | 4.80 ± 1.41 (29) | 10.40 ± 1.58 (25) | 4.02 ± 0.12 (16) | 4.61 ± 1.59 (11) |
| GABA | 0.11 ± 0.02 (1) | 0.15 ± 0.04 (1) | 0.21 ± 0.02 (1) | 0.30 ± 0.08 (1) |
| Pro | 0.86 ± 0.32 (5) | 1.25 ± 0.46 (3) | 1.17 ± 0.22 (5) | 0.64 ± 0.09 (2) |
| Others | 3.88 ± 0.67 (23) | 10.63 ± 1.61 (25) | 9.50 ± 0.51 (37) | 10.90 ± (27) |
| Total | 16.67 ± 3.66 (100) | 41.92 ± 7.20 (100)[b] | 25.22 ± 0.6 (100)[b] | 40.96 ± 4.73 (100)[b] |
| Total N (%) | 2.43 ± 0.16 | 2.84 ± 0.18[b] | 2.80 ± 0.16[b] | 2.77 ± 0.14[b] |

[a]Values are the mean of three plants ± SD. Relative amino acid proportions are given in parentheses.
[b]Significant changes in the amino acid content and N content compared to the WT at the 0.05 probability level.
[c]No significant changes compared to the WT.

In contrast with the VS, at the 55DAS stage of plant development, there was a marked increase in the leaf total amino acid content of the leaves of the three mutants. This increase was due in part to an increase in Asn and Glu contents, which were up to 20- and 10-fold higher respectively in the gln1-3/gln1-4 mutant.

An increase in the amount of total N was also observed in the leaves of the three mutants.

Xylem and Phloem Sap Collection

Phloem exudates were obtained using the technique described by King and Zeevaart (Plant Physiol., 53: 96-103, 1974). The leaves were cut off and re-cut under water before rapid immersion in the collection buffer. For each experiment, fully expanded leaves of three individual plants (WT and the three mutants) were placed separately in a solution of 10 mM Hepes, 10 mM EDTA (adjusted to pH 7.5 with NaOH), in a humid chamber (relative humidity >90%) and in the dark. Exudates were collected during 6 h from 10 am to 4 pm. The fresh weights of the leaves were then measured and the exudates stored at −80° C. Phloem exudates (in the EDTA solution) were adjusted to pH 2.1 and centrifuged to remove debris and EDTA, which precipitate at that pH.

The results are shown in Table 4.

TABLE 4

Amino Acid Concentration (μmol μL$^{-1}$) and Proportions (%)[a]

| Amino Acid | WT | gln1-4 | gln1-3 | gln1-3/1-4 |
|---|---|---|---|---|
| Asp | 81.1 ± 10.1(10 | 43.9 ± 8.4(13)[b] | 60.5 ± 6.8(16)[b] | 46.9 ± 4.6(14)[b] |
| Asn | 21.2 ± 10.5(3) | 5.2 ± 1.3(2)[b] | 2.6 ± 0.4(1)[b] | 4.3 ± 0.4(1)[b] |
| Glu | 79.5 ± 15.1(10)[c] | 46.8 ± 9.5(14)[c] | 79.5 ± 13(21)[c] | 56.3 ± 6.2(17)[c] |
| Gln | 159.8 ± 42.5(19) | 70.5 ± 19.4(21)[b] | 66 ± 32(18)[b] | 67.1 ± 6.6(20)[b] |
| Ala | 85.6 ± 1.4(4.6) | 22.1 ± 4.5(7)[b] | 10.9 ± 12(3)[b] | 18.3 ± 1.2(5)[b] |
| GABA | 48.0 ± 29.1(6) | 9.2 ± 5.3(3) | 4.9 ± 2.4(1) | 4.5 ± 1.1 (1) |
| Pro | 9.9 ± 2.1(1) | 5.2 ± 0.9(2)[b] | 2.8 ± 0.6(2)[b] | 2.8 ± 2.8(1)[b] |
| Others | 289.7 ± 24.7(35) | 116.3 ± 9.3(35) | 136.4. ± 10.8(38) | 126.8 ± 26(37) |
| Total | 825 ± 28.2(100) | 329 ± 64[b] | 367 ± 54(100)[b] | 335 ± 24(100)[b] |

[a]Values are the mean of three plants ± SD. Relative amino acid proportions are given in parentheses.
[b]Significant changes in the amino acid content compared to the WT at the 0.05 probability level.
[c]No significant changes compared to the WT.

Analysis of the phloem sap composition at the VS revealed that in the three mutants there was a general decrease in the concentration of all the main amino acids except for Glu. This decrease was approximately 2-fold for Asp, Gln, Pro and at least 4-fold for Asn and Ala. However, the relative proportions of the amino acids were not markedly modified except for Glu, for which a slight increase was observed. No marked changes were observed for the free amino acid content of the kernel, except a 2-fold decrease in Asn in the mutants, which represented about 14% of the total in the WT (data not shown).

In order to determine if the roots were able to provide enough N assimilates to the shoots in the three mutants, the amino acid composition of the xylem sap was analyzed. For xylem sap collection, stems of plants were cut 2 cm above the root system, and the cut stem was rinsed with water and blotted dry. Root pressure bleeding sap (about 200 to 400 μL per plant) was collected with a micropipette and the samples were immediately stored at −80° C. Amino acid analysis was performed as described previously. The results are shown in Table 5.

TABLE 5

Amino Acid Concentration (μmol μL$^{-1}$) and Proportions (%)[a]

| Amino Acid | WT | gln1-4 | gln1-3 | gln1-3/1-4 |
|---|---|---|---|---|
| Asp | 13.8 ± 7.8(7.8) | na[c] | 19.8 ± 2.8(17.1) | 13.6 ± 7.0(9.1) |
| Asn | 57.0 ± 18.5(32.1) | | 18.0 ± 4.2(15.5)[b] | 38 ± 13.6(25.5)[b] |
| Glu | 5.6 ± 2.5(3.1) | | 2.2 ± 0.4(1.8)[b] | 4.6 ± 1.8(3.0)[b] |
| Gln | 42.4 ± 8.5(23.9) | | 32.6 ± 3.2 (28.1)[b] | 35.6 ± 1.6(23.8)[b] |
| Ala | 8.2 ± 1.4(4.6) | | 1.0 ± 2(0.8) | 9.2 ± 2.8(6.1) |
| GABA | 1.0 ± 0.6(0.5) | | 0.2 ± 0.4(0.2) | 1.4 ± 1.0 (0.9) |
| Pro | 0 ± (0) | | 0 ± (0) | 0 ± (0) |
| Others | 49.4 ± 11.4(28) | | 42.4 ± 4.4(36.5) | 46.6 ± (31.6) |
| Total | 177.4 ± 8.9(100) | | 116.2 ± 2.0(100) | 149.0 ± 7.3(100) |

[a]Values are the mean of three plants ± SD. Relative amino acid proportions are given in parentheses.
[b]No significant changes in the amino acid content compared to the WT at the 0.05 probability level.
[c]Not available A slight decrease in the total amino acid concentration of the xylem sap at the VS was observed, particularly in gln1-3, due mainly to a decrease in Asn, the most abundant amino acid in the xylem sap. However this decrease was not significant. Interestingly, the amount of Gln, which is almost as abundant as Asn, was not significantly modified in the mutants compared to the WT.

Example 5

Overexpression of GS1

Plant Transformation, Regeneration and Characterization

Maize transformation of the inbred line A188 with *Agrobacterium tumefaciens* strain LBA4404 harbouring a super-binary plasmid was performed essentially as described by Ishida et al. (Nat. Biotechnol., 14: 745-750, 1996). In particular, the composition of all media cited hereafter is detailed in this reference. The protocol was slightly modified concerning the selective marker, which was the NPTII gene instead of the bar gene.

Super-Binary Plasmid pRec 445

The super-binary plasmid used for transformation was the result of a recombination between plasmid pBIOS 445 and the plasmid pSB1 (harbouring the virB and virG genes isolated from the super-virulent strain A281) within the

Figure 7:
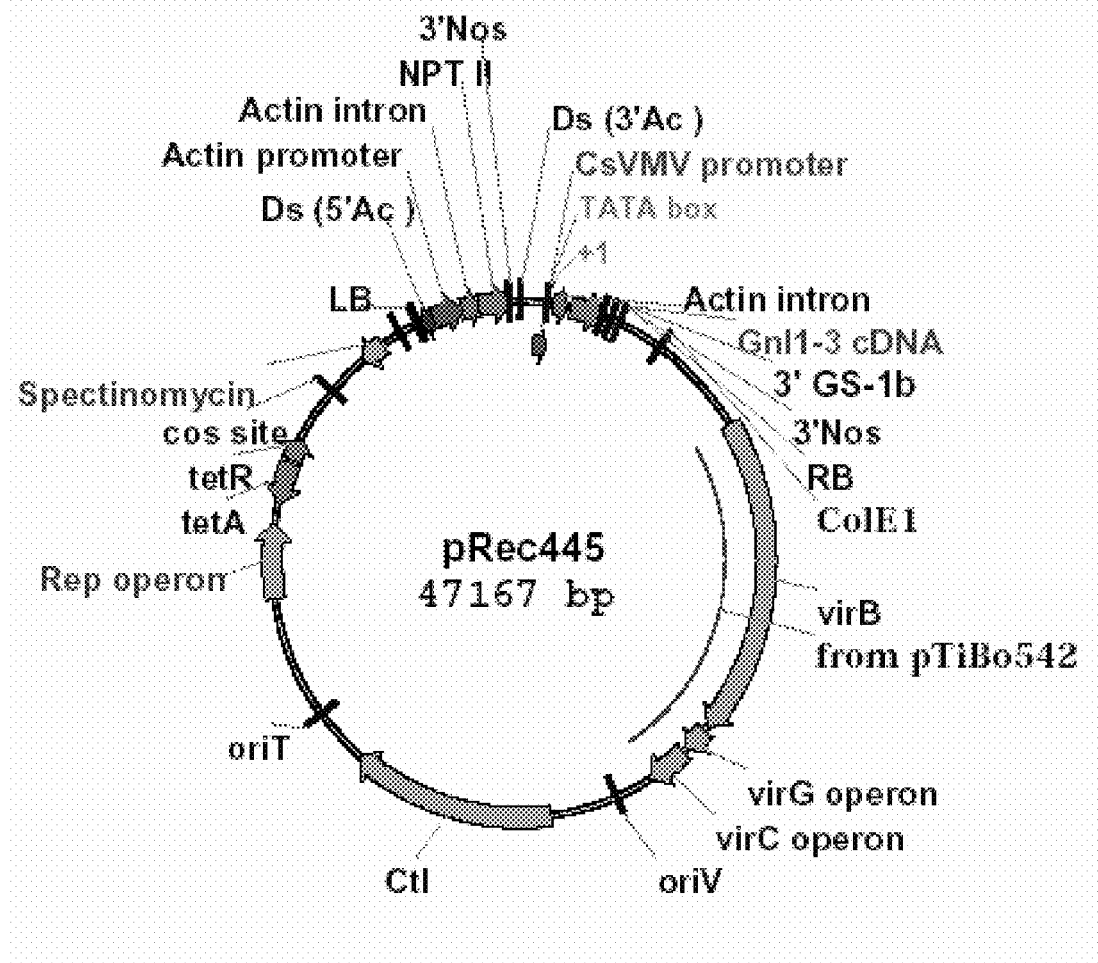
FIG. 7 depicts a schematic diagram of the pRec 445 plasmid used for *Agrobacterium*-mediated transformation of plants. The pRec 445 plasmid includes a neomycin resistance cassette and an expression cassette containing the Gln1-3 cDNA.

*agrobacterium* strain LBA4404 (pSB1) (Komari et al., Plant J., 10: 165-74, 1996) forming the plasmid pRec 445. pBIOS 445 is a derivative of pSB11 (Komari et al., aforementioned, 1996) harbouring between the T-DNA borders a neomycin resistance cassette (NPTII gene) (Bevan et al., Biotechnol., 24: 367-70, 1992; Berg and Berg, Biotechnol., 1: 417-435, 1983) flanked by an actin promoter (McElroy et al., Plant Cell, 2(2): 163, 1990), and 3'Nos terminator (Depicker et al., J. Mol. Appl. Genet., 1: 561-73, 1982) and the Gln1-3 cDNA (Sakakibara et al., aforementioned, 1992) flanked by the Cassava vein mosaic virus promoter (pCsVMV) (Verdaguer et al., Plant Mol. Biol., 6: 1129-39, 1996) linked to an actin intron (McElroy et al., aforementioned, 1990), and 3'Nos terminator. The resulting agrobacterial strain used for transformation was LB4404 (pRec 445).

pRec 445 is schematized in FIG. 7:

RB and LB represent the right and left borders of the T-DNA.

Ds (3'Ac) and Ds (5'Ac) represent the Ds transposable element used to further remove the selection marker conferring resistance to kanamycin.

NptII is the neomycin phosphotransferase gene with the Actin promoter and the Actin intron and nopaline synthetase terminator (3'Nos) conferring kanamycin resistance.

An Actin intron was placed between the maize Gln1-3 cDNA and the CsVMV promoter. The LB and RB extra borders, the 3'Nos, the Gln1-3 and the intron actin were used as probes to determine the pattern of the construct insertion events in the transgenic maize lines.

Transgenic Plants

Plant transformation was conducted using immature maize embryos isolated at 10 days after pollination. Immature embryos were incubated for 5 min with *A. tumefaciens* and cultured for 3 days on a LSAs medium without antibiotic selection in the dark at 25° C. Upon transfer to the LSD5 medium, *A. tumefaciens* was counter-selected by the presence of 250 mg L$^{-1}$ cefotaxime, and the transformed calli were selected by the presence of 50 mg µL$^{-1}$ kanamycin. After 2 weeks of culture, developing calli were transferred to LSD10 medium containing 50 mg µL$^{-1}$ kanamycin and grown for 3 weeks. Type I calli were excised and cultured for another 3 weeks on kanamycin. For regeneration, well-developed type I calli were cultured on LSZ medium at 22° C. under continuous selective pressure and on kanamycin. After 2 weeks, calli bearing shoots were transferred to RMG2 medium and cultured another 2 weeks to allow the development of roots before the transfer of the plantlets to soil and gradual acclimatization to ambient humidity. Plants were then cultivated in a glasshouse (18° C.-24° C.) and selfed or pollinated with line A188 to produce seeds.

A number of transgenic lines were selected and tested for the pattern of insertion of the pCsVMV-Gln1-3 construct. Following digestion of the genomic DNA with NcoI, hybridization was performed with: Gln1-3 cDNA, actin intron and 3'Nos probes in order to determine T-DNA copy number. In addition, two probes designed on the plasmid pRec 445 each overlapping the two RB and LB T-DNA borders in order to check the eventual presence of plasmids sequence external to the T-DNA (See FIG. 7 for the position of the probes). In two primary transformants (Line 1 and Line 9), a single insertion event was detected without the presence of additional T-DNA sequences, apart from those flanking the insert containing the pCsVMV-Gln1-3 and the pActin-NPTII chimeric constructs (data not shown). These two primary transformants were crossed to the line FV2, which contained the unfavourable allele for Gln1-3 (Hirel et al., aforementioned, 2001). T1 transformants were then selected and back-crossed three times with the line FV2. In the T4 generation containing 50% transgenics, the 50% null segregants for Line 1 and Line 9 were used as untransformed control plants and named WT1 and WT9 respectively.

The cDNA encoding Gln1-3 was made constitutive by fusing it with the CsVMV promoter. After selection and regeneration, followed by three back-crosses with the line FV2, two T4 transgenic plants (Line 1 and Line 9) overexpressing Gln1-3 and the corresponding null segregants (WT1 and WT9) were selected for further analysis.

Figure 8:
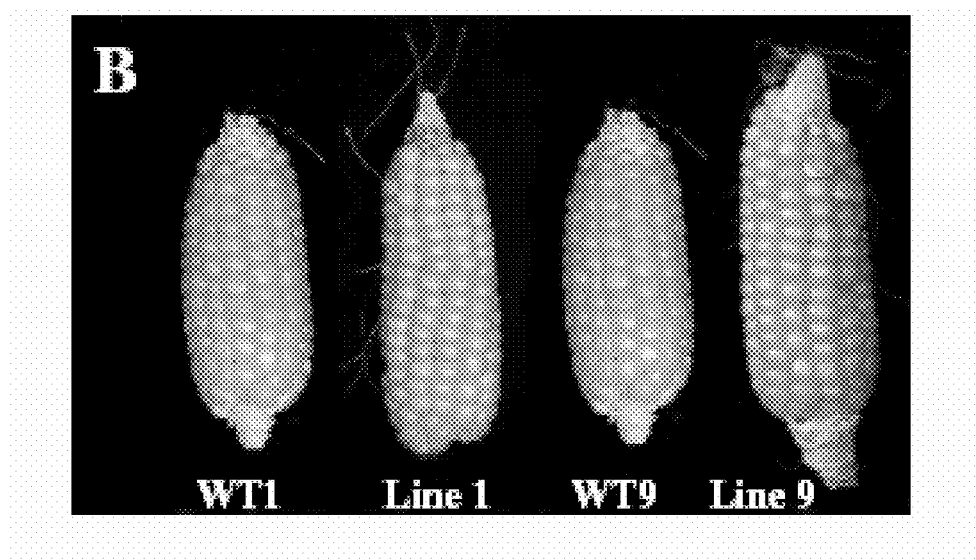
FIG. 8 depicts an image of ears of corn obtained from maize plants that overexpress the Gln1-3 cDNA (Line 1 and Line 9) and corresponding untransformed WT null segregants (WT1 and WT9).

These maize plants were grown under N suboptimal conditions on a nutrient solution containing 10 mM NO$_3^-$ and harvested at maturity. Ears of WT untransformed null segregants (WT1 and WT9) and T4 transgenic lines (Line 1 and Line 9) overexpressing the Gln1-3 cDNA are shown in FIG. 8.

It is to be noted that the ear in the untransformed WT plants was smaller compared to that of the untransformed null segregants (WT) shown in FIG. 6, to compare the phenotype of the mutants due to the fact that the European line FV2 produces fewer kernels than the North-American line B73, used for generating the transgenic maize plants.

Characterization of the Transgenic Plants

The impact of Gln1-3 overexpression on plant phenotype and kernel production was determined on plants grown in a glasshouse until maturity under suboptimal N feeding conditions.

GS Subunit Composition

The GS subunit composition of leaves at the VS of the two untransformed null segregants (WT1 and WT9) and the two transgenic lines (Line 1 and Line 9) was examined by Western blot analysis using the tobacco antibodies recognizing GS1 and GS2. The results are shown in FIG. 9.

Figure 9:
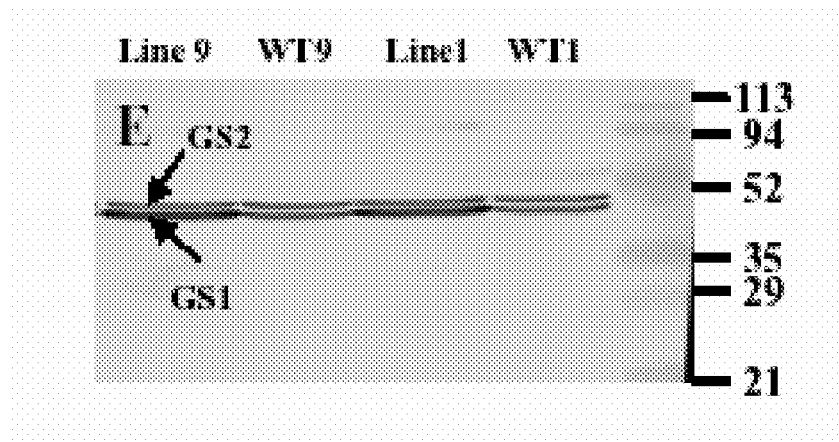
FIG. 9 depicts Western blot analysis of vegetative stage (VS) leaves obtained from maize plants that overexpress the Gln1-3 cDNA (Line 1 and Line 9) and corresponding untransformed WT null segregants (WT1 and WT9). The blot was stained with tobacco GS antibodies. The upper band (molecular mass of 44 kD) corresponds to the plastidic GS (GS2) subunit, and the lower band (molecular mass of 39 kD) correspond to the cytosolic GS (GS1) subunit.

Legend of FIG. 9:

The upper band (molecular mass of 44 kD) corresponds to the plastidic GS (GS2) subunit, and the lower band (molecular mass of 39 kD) correspond to the cytosolic GS (GS1) subunit.

An increase in the amount of GS1 protein was clearly visible in the protein extracts of the two transformed plants, that of Line 9 being noticeably higher. When the GS proteins were analyzed in the leaves 55DAS, a similar pattern of increase in GS1 protein content was obtained (data not shown).

Shoot and Grain Yield in Relation to GS Activity

Shoot and grain yield in relation to GS activity of the two untransformed null segregants (WT1 and WT9) and the two transgenic lines (Line 1 and Line 9) was determined. The results are shown in FIG. 10.

Figure 10:
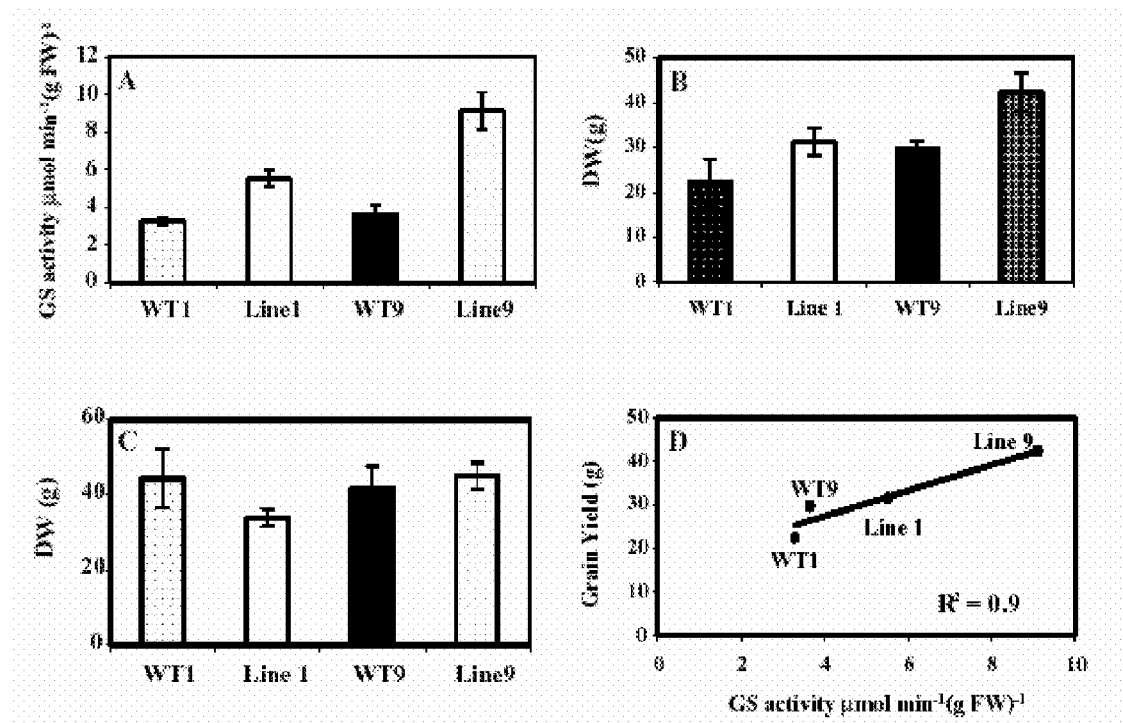
FIGS. 10A-D depict graphs showing the relationship between GS activity and shoot and grain yield in maize plants that overexpress the Gln1-3 cDNA (Line 1 and Line 9) and corresponding untransformed WT null segregants (WT1 and WT9).

Legend of FIG. 10:

A=total leaf GS activity

B=kernel yield

C=total dry weight of shoot vegetative parts

D=scatter plots between leaf GS activity (abscissa) and kernel yield (ordinate).

Compared to the two untransformed null segregants, a two and three fold increase in total leaf GS activity was observed in Lines 1 and 9 respectively (FIG. 10A).

A significant increase in kernel yield was observed, which when compared to two corresponding WT control plants was approximately 30% for both Line 1 and Line 9 (FIG. 10B), thus confirming the phenotype shown in FIG. 8. Kernel number was the yield component that was mostly responsible for the increase in kernel production, as shown below in Table 6.

TABLE 6

| | Grain Yield (g) | Grain Number | Thousand Kernels Weight (g) | Grain N content (% DW) |
|---|---|---|---|---|
| WT(line F2) | 26.05 ± 3.5(100) | 102.5 ± 17.4(100) | 259.9 ± 8.2(100) | 2.16 ± 0.02 (100) |
| CsVMV-Gln1-3 | 36.9 ± 3.8(142)[a] | 127.9 ± 13.6(125)[a] | 276.9 ± 6.7(106) | 2.19 ± 0.06 (101) |

Each value is the mean ± SE obtained from six individual plants.
The values indicated in parentheses are expressed as percentage of the value in the WT (the mean of the two transgenic lines and of the corresponding null segregants)

Linear regression and the resulting correlation coefficient were calculated for the level of leaf GS activity versus grain yield in the two untransformed null segregants and the two transgenic lines. FIG. 10D, shows that there is a strong relationship between leaf GS activity and grain yield ($r^2$ 0.91), thus indicating that the increase in yield is proportional to the increase in enzyme activity.

In contrast, no significant differences were seen in shoot dry matter production between the two WT control plants and the two transgenic lines (FIG. 10C).

Example 6

Overexpression of GS1 in Leaf Mesophyll and Bundle-Sheath Cells

As described in example 5, expression of GS1-3 from the pCsVMV promoter results in significantly increased GS activity in transformed plants and improves agronomic performance. However expression of pCsVMV is largely confined to mesophyll cells, thus expression of GS1 in transformed maize plant leaves can be further optimised by the use of promoters that direct high level expression both in the mesophyll and bundle sheath cells. An alternative strategy, described below, is to transform maize with a T-DNA expressing GS1-3 under control of the pCsVMV promoter, together with GS1-4 under the control of a bundle-sheath cell specific promoter such as maize rbcS promoter (Katayama et al., aforementioned, 2000), in order to obtain transgenic maize plants expressing GS1-3 in the mesophyll and GS1-4 in the bundle sheath cells. It is expected that grain yields are improved in said transgenic plants, both in N-limiting and non-limiting conditions.

Plant Transformation, Regeneration and Characterization

Maize transformation of the inbred line A188 with *Agrobacterium tumefaciens* strain LBA4404 harbouring a super-binary plasmid was performed essentially as described by Ishida et al. (aforementioned, 1996). In particular, the composition of all media cited hereafter is detailed in this reference. The only modification concerns the selective marker, which is the NPTII gene in the present example, instead of the bar gene used by Ishida et al.

Super-Binary Plasmid pRec 445+

The super-binary plasmid used for transformation is the result of a recombination between the plasmid pBIOS 445+ and the plasmid pSB1 (harbouring the virB and virG genes isolated from the super-virulent strain A281) within the *Agrobacterium* strain LBA4404 (pSB1) (Komari et al., aforementioned, 1996) forming the plasmid pRec 445. (pBIOS 445+ is identical to pBIOS 445 (example 5) except that it also contains between the T-DNA borders, a maize rbcS promoter (Katayama et al., aforementioned, 2000) linked to Gln1-4 cDNA and a nos terminator. The resulting agrobacterial strain used for transformation was LB4404 (pRec 445+).

What is claimed:

1. A method for producing kernels from a cereal plant, wherein said method comprises:
   (a) growing a transgenic cereal plant comprising a recombinant cassette comprising a polynucleotide encoding the maize glutamine synthetase GS1-3 isoenzyme having the sequence SEQ ID NO: 2, wherein said transgenic cereal plant overexpresses said GS1-3 isoenzyme when compared to a non-transgenic cereal plant, and wherein said overexpression results in an increased number of kernels when compared to said non-transgenic cereal plant, and wherein the transgenic cereal plant is grown under N suboptimal conditions, and
   (b) harvesting the kernels from said transgenic cereal plant.

2. The method according to claim 1, wherein the transgenic cereal plant is selected from the group consisting of a transgenic wheat plant, a transgenic rice plant or a transgenic maize plant.

3. The method according to claim 1, wherein the transgenic cereal plant is a transgenic maize plant.

4. The method according to claim 1, wherein the kernels are harvested at maturity.

* * * * *

SEQUENCE LISTING

```
<160> NUMBER OF SEQ ID NOS: 10

<210> SEQ ID NO 1
<211> LENGTH: 1317
<212> TYPE: DNA
<213> ORGANISM: Zea mays
<220> FEATURE:
<221> NAME/KEY: CDS
<222> LOCATION: (63)..(1133)

<400> SEQUENCE: 1
caatcccaca ccaccaccac ctcctccggt ccccaacccc tgtcgcaccg cagccgccgg      60 cc atg gcc tgc ctc acc gac ctc gtc aac ctc aac ctc tcg gac acc       107
   Met Ala Cys Leu Thr Asp Leu Val Asn Leu Asn Leu Ser Asp Thr
   1               5                   10                  15 acc gag aag atc atc gcg gaa tac ata tgg atc ggt gga tct ggc atg      155
Thr Glu Lys Ile Ile Ala Glu Tyr Ile Trp Ile Gly Gly Ser Gly Met
                20                  25                  30 gat ctc agg agc aaa gca agg acc ctc tcc ggc ccg gtg acc gat ccc      203
Asp Leu Arg Ser Lys Ala Arg Thr Leu Ser Gly Pro Val Thr Asp Pro
            35                  40                  45 agc aag ctg ccc aag tgg aac tac gac ggc tcc agc acg ggc cag gcc      251
Ser Lys Leu Pro Lys Trp Asn Tyr Asp Gly Ser Ser Thr Gly Gln Ala
        50                  55                  60 ccc ggc gag gac agc gag gtc atc ctg tac ccg cag gcc atc ttc aag      299
Pro Gly Glu Asp Ser Glu Val Ile Leu Tyr Pro Gln Ala Ile Phe Lys
    65                  70                  75 gac cca ttc agg agg ggc aac aac atc ctt gtg atg tgc gat tgc tac      347
```

```
Asp Pro Phe Arg Arg Gly Asn Asn Ile Leu Val Met Cys Asp Cys Tyr
 80              85                  90                  95 acc cca gcc ggc gag cca atc ccc acc aac aag agg tac aac gcc gcc        395
Thr Pro Ala Gly Glu Pro Ile Pro Thr Asn Lys Arg Tyr Asn Ala Ala
                100                 105                 110 aag atc ttc agc agc cct gag gtc gcc gcc gag gag ccg tgg tat ggt        443
Lys Ile Phe Ser Ser Pro Glu Val Ala Ala Glu Glu Pro Trp Tyr Gly
            115                 120                 125 att gag cag gag tac acc ctc ctc cag aag gac acc aac tgg ccc ctt        491
Ile Glu Gln Glu Tyr Thr Leu Leu Gln Lys Asp Thr Asn Trp Pro Leu
        130                 135                 140 ggg tgg ccc atc ggt ggc ttc ccc ggc cct cag ggt cct tac tac tgt        539
Gly Trp Pro Ile Gly Gly Phe Pro Gly Pro Gln Gly Pro Tyr Tyr Cys
    145                 150                 155 gga atc ggc gcc gaa aag tcg ttc ggc cgc gac atc gtg gac gcc cac        587
Gly Ile Gly Ala Glu Lys Ser Phe Gly Arg Asp Ile Val Asp Ala His
160                 165                 170                 175 tac aag gcc tgc ttg tat gcg ggc atc aac atc agt ggc atc aac ggg        635
Tyr Lys Ala Cys Leu Tyr Ala Gly Ile Asn Ile Ser Gly Ile Asn Gly
                180                 185                 190 gag gtg atg cca ggg cag tgg gag ttc caa gtc ggg cct tcc gtg ggt        683
Glu Val Met Pro Gly Gln Trp Glu Phe Gln Val Gly Pro Ser Val Gly
            195                 200                 205 att tct tca ggc gac cag gtc tgg gtc gct cgc tac att ctt gag agg        731
Ile Ser Ser Gly Asp Gln Val Trp Val Ala Arg Tyr Ile Leu Glu Arg
        210                 215                 220 atc acg gag atc gcc ggt gtg gtg gtg acg ttc gac ccg aag ccg atc        779
Ile Thr Glu Ile Ala Gly Val Val Val Thr Phe Asp Pro Lys Pro Ile
    225                 230                 235 ccg ggc gac tgg aac ggc gcc ggc gcg cac acc aac tac agc acg gag        827
Pro Gly Asp Trp Asn Gly Ala Gly Ala His Thr Asn Tyr Ser Thr Glu
240                 245                 250                 255 tcg atg agg aag gag ggc ggg tac gag gtg atc aag gcg gcc atc gag        875
Ser Met Arg Lys Glu Gly Gly Tyr Glu Val Ile Lys Ala Ala Ile Glu
                260                 265                 270 aag ctg aag ctg cgg cac agg gag cac atc gcg gcc tac ggc gag ggc        923
Lys Leu Lys Leu Arg His Arg Glu His Ile Ala Ala Tyr Gly Glu Gly
            275                 280                 285 aac gac ggc cgg ctc acc ggc agg cac gag acc gcc gac atc aac acg        971
Asn Asp Gly Arg Leu Thr Gly Arg His Glu Thr Ala Asp Ile Asn Thr
        290                 295                 300 ttc agc tgg ggc gtg gcc aac cgc ggc gcg tcg gtg cgc gtg ggc cgg       1019
Phe Ser Trp Gly Val Ala Asn Arg Gly Ala Ser Val Arg Val Gly Arg
    305                 310                 315 gag acg gag cag aac ggc aag ggc tac ttc gag gac cgc cgc ccg gcg       1067
Glu Thr Glu Gln Asn Gly Lys Gly Tyr Phe Glu Asp Arg Arg Pro Ala
320                 325                 330                 335 tcc aac atg gac ccc tac gtg gtc acc tcc atg atc gcc gag acc acc       1115
Ser Asn Met Asp Pro Tyr Val Val Thr Ser Met Ile Ala Glu Thr Thr
                340                 345                 350 atc atc tgg aag ccc tga gcgccgcggc cgttgcgttg cagggtcccc              1163
Ile Ile Trp Lys Pro
            355 gaagcgattg caaagccact gttccttccg ttctgtttgc ttattattgt tattatctag     1223 ctagatcatc cggggtcagg tcgtcgtggt gtgccaaaac agaacacaga aagaggaaga     1283 agaaaaaaaa aacaagacgt gtggcgttta tgtt                                 1317

<210> SEQ ID NO 2
```

```
<211> LENGTH: 356
<212> TYPE: PRT
<213> ORGANISM: Zea mays

<400> SEQUENCE: 2

Met Ala Cys Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Asn Ala Ala Lys
            100                 105                 110

Ile Phe Ser Ser Pro Glu Val Ala Ala Glu Pro Trp Tyr Gly Ile
        115                 120                 125

Glu Gln Glu Tyr Thr Leu Leu Gln Lys Asp Thr Asn Trp Pro Leu Gly
    130                 135                 140

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ser Gly Asp Gln Val Trp Val Ala Arg Tyr Ile Leu Glu Arg Ile
    210                 215                 220

Thr Glu Ile Ala Gly Val Val Val Thr Phe Asp Pro Lys Pro Ile Pro
225                 230                 235                 240

Gly Asp Trp Asn Gly Ala Gly Ala His Thr Asn Tyr Ser Thr Glu Ser
                245                 250                 255

Met Arg Lys Glu Gly Gly Tyr Glu Val Ile Lys Ala Ala Ile Glu Lys
            260                 265                 270

Leu Lys Leu Arg His Arg Glu His Ile Ala Ala Tyr Gly Glu Gly Asn
        275                 280                 285

Asp Gly Arg Leu Thr Gly Arg His Glu Thr Ala Asp Ile Asn Thr Phe
    290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
            340                 345                 350

Ile Trp Lys Pro
        355

<210> SEQ ID NO 3
<211> LENGTH: 1490
<212> TYPE: DNA
```

```
<213> ORGANISM: Zea mays
<220> FEATURE:
<221> NAME/KEY: CDS
<222> LOCATION: (85)..(1152)

<400> SEQUENCE: 3
ccacatcctc ccctcattcc tccttgggtt cccagcccgt gcgccccgcc tgtcgcagtg      60
ccagtcgcgc cgcagccgcc ggcc atg gcc tgc ctc acc gac ctc gtc aac        111
                           Met Ala Cys Leu Thr Asp Leu Val Asn
                             1               5 ctc aac ctc tcg gac acc aca gag aag atc atc gcc gag tac ata tgg       159
Leu Asn Leu Ser Asp Thr Thr Glu Lys Ile Ile Ala Glu Tyr Ile Trp
 10              15                  20                  25 atc ggt gga tct ggc atg gat ctc agg agc aaa gcc agg acc ctc ccg       207
Ile Gly Gly Ser Gly Met Asp Leu Arg Ser Lys Ala Arg Thr Leu Pro
                 30                  35                  40 ggc ccg gtg acc gat ccc agc aag ctg ccc aag tgg aac tac gac ggc       255
Gly Pro Val Thr Asp Pro Ser Lys Leu Pro Lys Trp Asn Tyr Asp Gly
             45                  50                  55 tcc agc acc ggc cag gcc ccc ggc gag gac agc gag gtc atc ctg tac       303
Ser Ser Thr Gly Gln Ala Pro Gly Glu Asp Ser Glu Val Ile Leu Tyr
         60                  65                  70 ccg cag gcc atc ttc aag gac cca ttc agg agg ggc aac aac atc ctt       351
Pro Gln Ala Ile Phe Lys Asp Pro Phe Arg Arg Gly Asn Asn Ile Leu
     75                  80                  85 gtc atg tgc gat tgc tac acc cca gct ggc gag cca att ccc acc aac       399
Val Met Cys Asp Cys Tyr Thr Pro Ala Gly Glu Pro Ile Pro Thr Asn
 90                  95                 100                 105 aag agg tac agc gcc gcc aag atc ttc agc agc cct gag gtc gct gcc       447
Lys Arg Tyr Ser Ala Ala Lys Ile Phe Ser Ser Pro Glu Val Ala Ala
                110                 115                 120 gag gag ccc tgg tat ggt atc gag cag gag tac acc ctc ctt cag aag       495
Glu Glu Pro Trp Tyr Gly Ile Glu Gln Glu Tyr Thr Leu Leu Gln Lys
            125                 130                 135 gac acc aac tgg ccc ctc ggg tgg cct att ggc ggc ttc cct ggc cct       543
Asp Thr Asn Trp Pro Leu Gly Trp Pro Ile Gly Gly Phe Pro Gly Pro
        140                 145                 150 cag ggt cct tac tac tgt gga atc ggc gcg gag aaa tcg ttc ggg cgt       591
Gln Gly Pro Tyr Tyr Cys Gly Ile Gly Ala Glu Lys Ser Phe Gly Arg
    155                 160                 165 gac ata gtc gac gcc cac tac aag gcc tgc ctg tac gca ggc atc aac       639
Asp Ile Val Asp Ala His Tyr Lys Ala Cys Leu Tyr Ala Gly Ile Asn
170                 175                 180                 185 atc agt ggc atc aac ggg gag gtc atg ccg ggg cag tgg gag ttc cag       687
Ile Ser Gly Ile Asn Gly Glu Val Met Pro Gly Gln Trp Glu Phe Gln
                190                 195                 200 gtc gga ccg tcc gtc ggc atc tct tcg ggc gat cag gtg tgg gtt gct       735
Val Gly Pro Ser Val Gly Ile Ser Ser Gly Asp Gln Val Trp Val Ala
            205                 210                 215 cgc tac att ctt gag agg atc acc gag atc gcc ggc gtg gtg gtg acg       783
Arg Tyr Ile Leu Glu Arg Ile Thr Glu Ile Ala Gly Val Val Val Thr
        220                 225                 230 ttc gac ccg aag ccg atc ccg ggc gac tgg aac ggc gcg ggc gcc cac       831
Phe Asp Pro Lys Pro Ile Pro Gly Asp Trp Asn Gly Ala Gly Ala His
    235                 240                 245 acc aac tac agc acc gag tcc atg agg aag gag ggc ggg tac gag gtg       879
Thr Asn Tyr Ser Thr Glu Ser Met Arg Lys Glu Gly Gly Tyr Glu Val
250                 255                 260                 265 atc aag gcg gcc atc gag aag ctg aag ctg cgg cac aag gag cac atc       927
Ile Lys Ala Ala Ile Glu Lys Leu Lys Leu Arg His Lys Glu His Ile
```

```
                   270                 275                 280
gcg gcc tac ggc gag ggc aac gag cgc cgg ctc acc ggc agg cac gag    975
Ala Ala Tyr Gly Glu Gly Asn Glu Arg Arg Leu Thr Gly Arg His Glu
            285                 290                 295 acc gcc gac atc aac acc ttc agc tgg gga gtc gcc aac cgt ggc gcg   1023
Thr Ala Asp Ile Asn Thr Phe Ser Trp Gly Val Ala Asn Arg Gly Ala
        300                 305                 310 tcg gtg gcc gtg ggc cag acg gag cag aac ggc aag ggc tac ttc gag   1071
Ser Val Ala Val Gly Gln Thr Glu Gln Asn Gly Lys Gly Tyr Phe Glu
    315                 320                 325 gac cgc cgg ccg gcg tcc aac atg gat ccc tac gtg gtc acc tcc atg   1119
Asp Arg Arg Pro Ala Ser Asn Met Asp Pro Tyr Val Val Thr Ser Met
330                 335                 340                 345 atc gcc gag acc acc atc gtc tgg aag ccc tga ggcatcccgt ggccgtgtcg 1172
Ile Ala Glu Thr Thr Ile Val Trp Lys Pro
                350                 355 tgtcggtttg ctccgcgtac ggcgctggcc gttgcatcgc agggcccagc ggttgcgcaa 1232 ctatttccc ttccccgttc cgtttgcttg tactactact ctaccgctag tcctgcatag  1292
cattttagct agaacacaac aacagccaaa aaaaaacatt gttgcttgct tcgacttcga 1352 cgcttcccac cactagttcc attccatgcc gtccgtccac ttccttcctg tgtaatcctc 1412 ctccaataat agacgtgtca tgctgcatcc tctgcattgt ataaaagaaa gtggtgtaat 1472 ccttttgctg gcgcctcc                                              1490

<210> SEQ ID NO 4
<211> LENGTH: 355
<212> TYPE: PRT
<213> ORGANISM: Zea mays

<400> SEQUENCE: 4

Met Ala Cys Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Ser Ala Ala Lys
            100                 105                 110

Ile Phe Ser Ser Pro Glu Val Ala Ala Glu Pro Trp Tyr Gly Ile
        115                 120                 125

Glu Gln Glu Tyr Thr Leu Leu Gln Lys Asp Thr Asn Trp Pro Leu Gly
    130                 135                 140

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
```

```
            195                 200                 205
    Ser Ser Gly Asp Gln Val Trp Val Ala Arg Tyr Ile Leu Glu Arg Ile
        210                 215                 220

Thr Glu Ile Ala Gly Val Val Thr Phe Asp Pro Lys Pro Ile Pro
    225                 230                 235                 240

Gly Asp Trp Asn Gly Ala Gly Ala His Thr Asn Tyr Ser Thr Glu Ser
                    245                 250                 255

Met Arg Lys Glu Gly Gly Tyr Glu Val Ile Lys Ala Ala Ile Glu Lys
                260                 265                 270

Leu Lys Leu Arg His Lys Glu His Ile Ala Ala Tyr Gly Glu Gly Asn
                275                 280                 285

Glu Arg Arg Leu Thr Gly Arg His Glu Thr Ala Asp Ile Asn Thr Phe
                290                 295                 300

Ser Trp Gly Val Ala Asn Arg Gly Ala Ser Val Ala Val Gly Gln Thr
    305                 310                 315                 320

Glu Gln Asn Gly Lys Gly Tyr Phe Glu Asp Arg Arg Pro Ala Ser Asn
                    325                 330                 335

Met Asp Pro Tyr Val Val Thr Ser Met Ile Ala Glu Thr Thr Ile Val
                340                 345                 350

Trp Lys Pro
        355

<210> SEQ ID NO 5
<211> LENGTH: 11
<212> TYPE: PRT
<213> ORGANISM: Zea mays

<400> SEQUENCE: 5

Thr Leu Ser Gly Pro Val Thr Asp Pro Ser Lys
1               5                   10

<210> SEQ ID NO 6
<211> LENGTH: 14
<212> TYPE: PRT
<213> ORGANISM: Zea mays

<400> SEQUENCE: 6

Thr Leu Ser Gly Pro Val Thr Asp Pro Ser Lys Leu Pro Lys
1               5                   10

<210> SEQ ID NO 7
<211> LENGTH: 11
<212> TYPE: PRT
<213> ORGANISM: Zea mays

<400> SEQUENCE: 7

Thr Leu Pro Gly Pro Val Thr Asp Pro Ser Lys
1               5                   10

<210> SEQ ID NO 8
<211> LENGTH: 14
<212> TYPE: PRT
<213> ORGANISM: Zea mays

<400> SEQUENCE: 8

Thr Leu Pro Gly Pro Val Thr Asp Pro Ser Lys Leu Pro Lys
1               5                   10

<210> SEQ ID NO 9
<211> LENGTH: 14
```

```
<212> TYPE: PRT
<213> ORGANISM: Zea mays

<400> SEQUENCE: 9

His Arg Glu His Ile Ala Ala Tyr Gly Glu Gly Asn Glu Arg
1               5                   10

<210> SEQ ID NO 10
<211> LENGTH: 14
<212> TYPE: PRT
<213> ORGANISM: Zea mays

<400> SEQUENCE: 10

His Lys Glu His Ile Ala Ala Tyr Gly Glu Gly Asn Glu Arg
1               5                   10
```